(12) United States Patent
Carter et al.

(10) Patent No.: US 11,759,548 B1
(45) Date of Patent: Sep. 19, 2023

(54) DEMINERALIZED BONE FIBER IMPLANT COMPOSITIONS AND METHODS FOR ROTATOR CUFF AND ACL REPAIR

(71) Applicant: TETROUS, INC., Sherman Oaks, CA (US)

(72) Inventors: Andrew J. Carter, Sherman Oaks, CA (US); Bradley E. Patt, Sherman Oaks, CA (US); Gunnar Andersson, Sherman Oaks, CA (US); Ian McRury, Sherman Oaks, CA (US); Nikhil Verma, Sherman Oaks, CA (US); Nelson L. Scarborough, Sherman Oaks, CA (US)

( * ) Notice: Subject to any disclaimer, the term of this patent is extended or adjusted under 35 U.S.C. 154(b) by 0 days.

(21) Appl. No.: 18/179,916

(22) Filed: Mar. 7, 2023

Related U.S. Application Data

(63) Continuation of application No. 17/429,561, filed as application No. PCT/US2020/017369 on Feb. 7, 2020, now Pat. No. 11,660,373.

(60) Provisional application No. 62/901,935, filed on Sep. 18, 2019, provisional application No. 62/803,470, filed on Feb. 9, 2019.

(51) Int. Cl.
| | |
|---|---|
| *A61L 27/36* | (2006.01) |
| *A61B 17/68* | (2006.01) |
| *A61B 17/04* | (2006.01) |
| *A61F 2/30* | (2006.01) |
| *A61B 17/88* | (2006.01) |
| *A61B 17/86* | (2006.01) |
| *A61L 27/56* | (2006.01) |
| *A61L 27/58* | (2006.01) |

(Continued)

(52) U.S. Cl.
CPC ...... *A61L 27/3608* (2013.01); *A61B 17/0401* (2013.01); *A61B 17/686* (2013.01); *A61B 17/86* (2013.01); *A61B 17/8897* (2013.01); *A61F 2/30965* (2013.01); *A61L 27/365* (2013.01); *A61L 27/3695* (2013.01); *A61L 27/56* (2013.01); *A61L 27/58* (2013.01); *A61B 17/16* (2013.01); *A61F 2/28* (2013.01); *A61F 2002/2835* (2013.01); *A61F 2002/30205* (2013.01); *A61F 2002/30224* (2013.01); *A61F 2002/30235* (2013.01)

(58) Field of Classification Search
CPC .......................... A61L 27/3608; A61B 17/686
See application file for complete search history.

(56) References Cited

U.S. PATENT DOCUMENTS 5,522,846 A * 6/1996 Bonutti ............. A61B 17/0401
606/232
5,984,926 A * 11/1999 Jones ................... A61B 17/686
606/76

(Continued)

OTHER PUBLICATIONS

International Search Report and Written Opinion dated May 12, 2020 in PCT/US2020/017369, 7 pages. (Year: 2020).*

*Primary Examiner* — Christian A Sevilla
(74) *Attorney, Agent, or Firm* — Squire Patton Boggs (US) LLP

(57) ABSTRACT

A composition and methods of making or use thereof include a plurality of fibers forming a shape for augmenting tendon to bone repair. The physical presence of the plurality of fibers provides initial fixation, while the use of an osteoinductive material provides long term enhancement of bone formation around the site of the tendon to bone repair.

22 Claims, 28 Drawing Sheets

(51) Int. Cl.
*A61B 17/16* (2006.01)
*A61F 2/28* (2006.01)

(56) References Cited

U.S. PATENT DOCUMENTS

| | | | |
|---|---|---|---|
| 6,193,516 B1* | 2/2001 | Story | A61C 8/0086 |
| | | | 433/201.1 |
| 2001/0002440 A1* | 5/2001 | Bonutti | A61B 17/0401 |
| | | | 606/232 |
| 2001/0008971 A1* | 7/2001 | Schwartz | A61B 17/0487 |
| | | | 606/232 |
| 2006/0040894 A1* | 2/2006 | Hunter | A61P 27/06 |
| | | | 514/495 |
| 2007/0270812 A1* | 11/2007 | Peckham | A61B 17/7068 |
| | | | 606/279 |
| 2009/0157181 A1* | 6/2009 | Osman | A61F 2/28 |
| | | | 606/151 |
| 2012/0288825 A1* | 11/2012 | Nordin | A61C 8/0069 |
| | | | 433/173 |
| 2015/0230889 A1* | 8/2015 | Kim | A61C 8/0013 |
| | | | 433/174 |
| 2018/0169295 A1* | 6/2018 | Yang | A61L 24/043 |

\* cited by examiner

FIG. 8
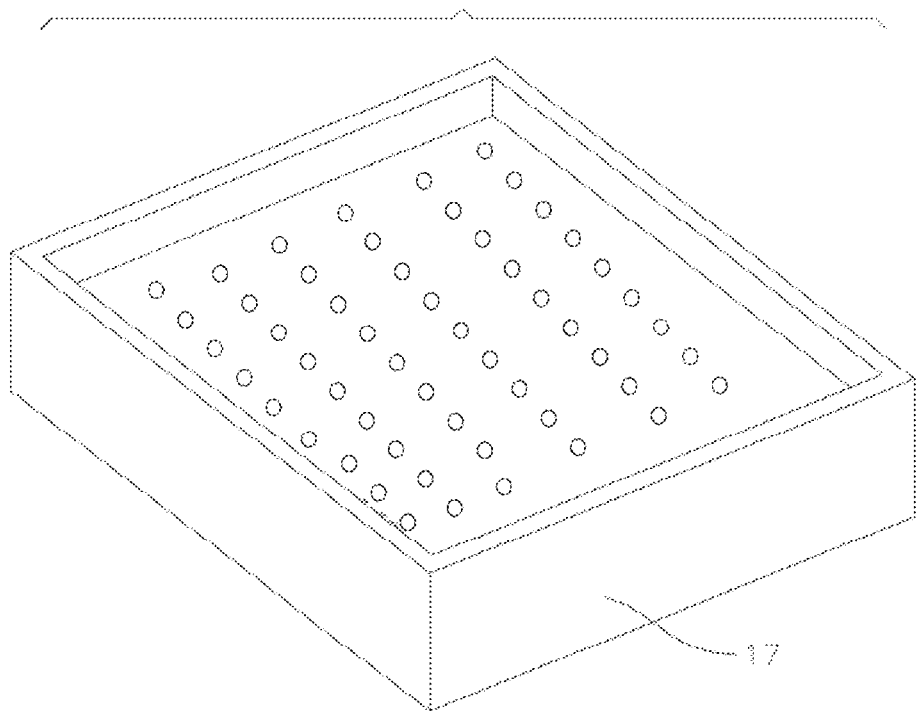
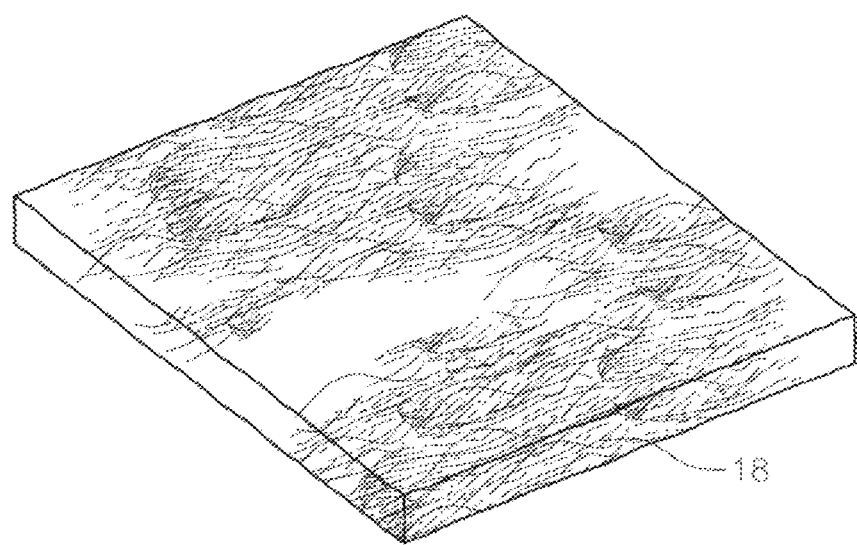

FIG. 25a
Components
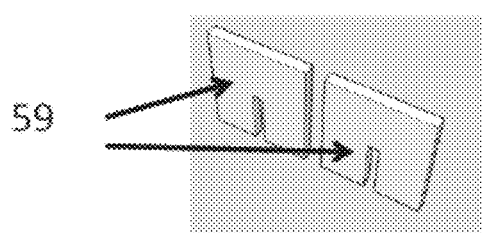
FIG. 25c
Positioning in Graft
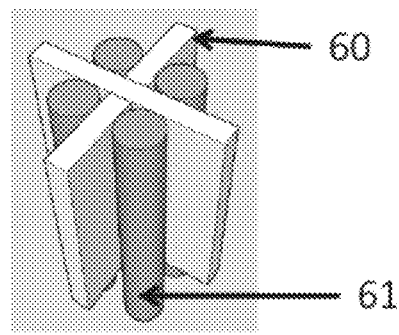
FIG. 25b Assembly
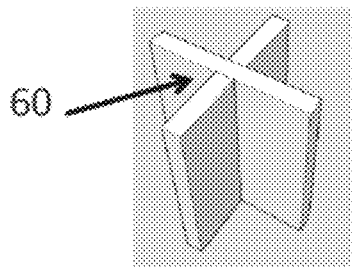
FIG. 25d
Final
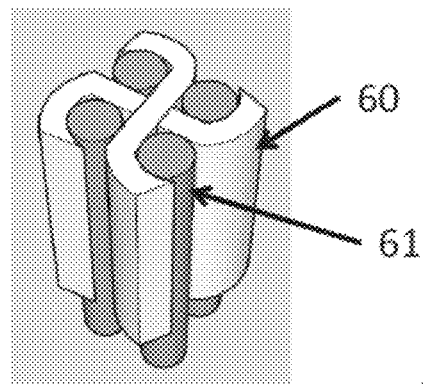
FIG. 25e Graft
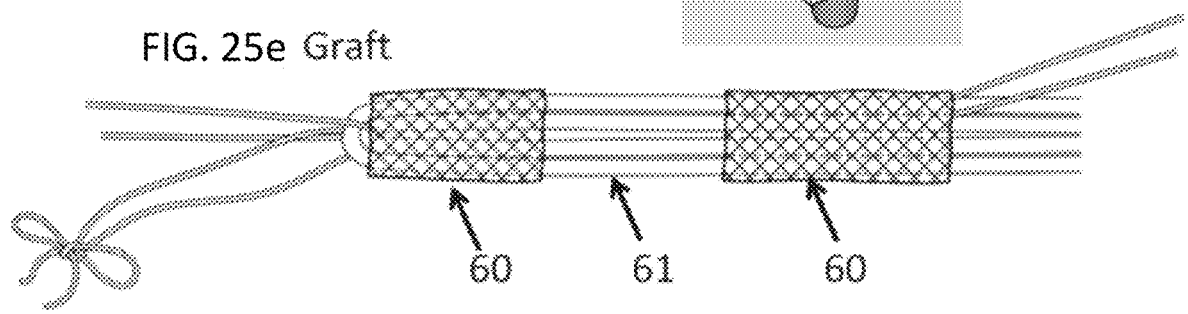

FIG. 26a Components
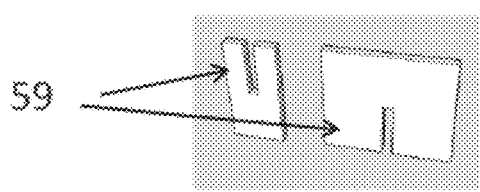
FIG. 26c Positioning in Graft
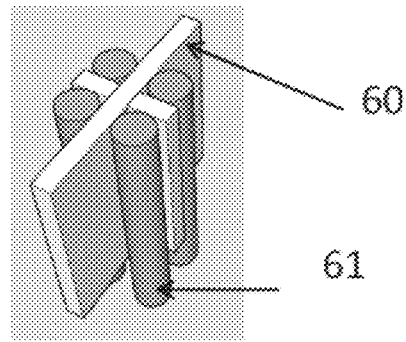
FIG. 26b Assembly
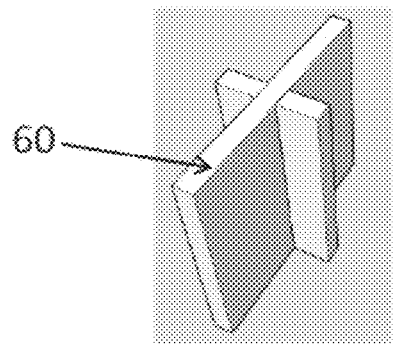
FIG. 26d Final
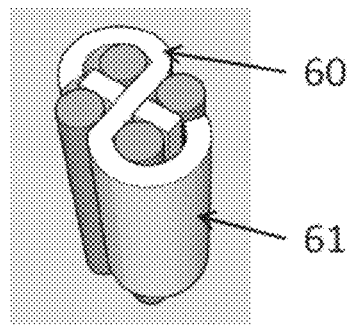
FIG. 26e Graft
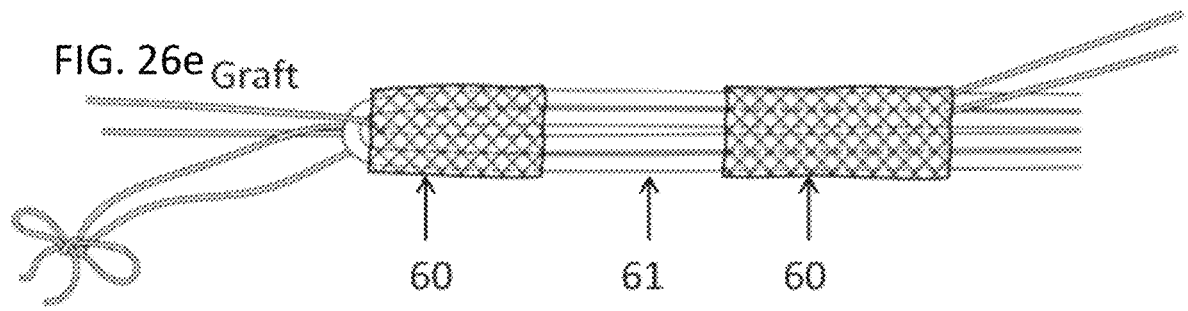

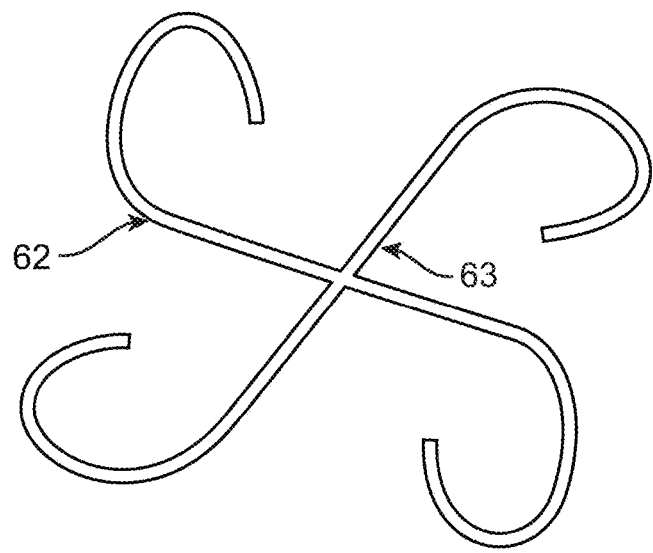
FIG. 27a
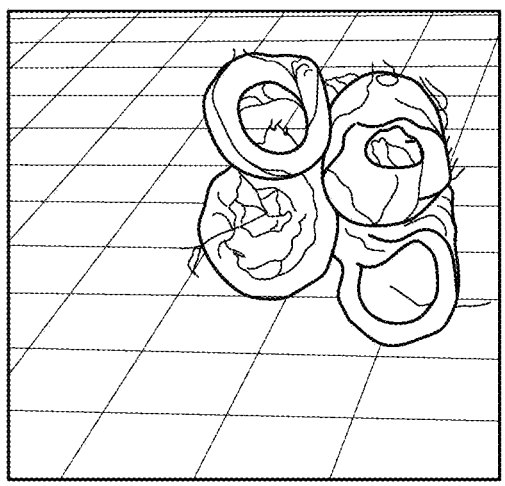 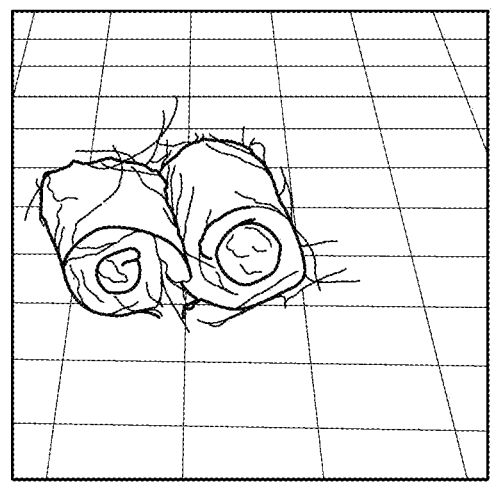
FIG. 27b　　　　FIG. 27c

DEMINERALIZED BONE FIBER IMPLANT COMPOSITIONS AND METHODS FOR ROTATOR CUFF AND ACL REPAIR

CROSS-REFERENCE TO RELATED APPLICATIONS

The present application is a continuation application of U.S. application Ser. No. 17/429,561, filed on Aug. 9, 2021, as a 35 U.S.C. § 371 national-phase filing of International Application No. PCT/US20/17369, filed on Feb. 7, 2020, which claims the benefit of U.S. Provisional Application No. 62/803,470, filed on Feb. 9, 2019 and U.S. Provisional Application No. 62/901,935, filed on Sep. 18, 2019, the entire contents of all of which are herein incorporated by reference.

FIELD OF THE INVENTION

The field of the invention relates to composition and methods of bone fiber implants made from cortical bone in which a plurality of demineralized bone fibers forms a shape having a peg portion and a sheet portion to augment tendon to bone repair.

BACKGROUND

The background description includes information that may be useful in understanding the present disclosure. It is not an admission that any of the information provided herein is prior art or relevant to the presently claimed invention, or that any publication specifically or implicitly referenced is prior art.

All publications and patent applications herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

Worldwide, osteoporosis causes more than 8.9 million fractures annually, resulting in an osteoporotic fracture every 3 seconds. Osteoporosis is estimated to affect 200 million women worldwide—approximately one-tenth of women aged 60, one-fifth of women aged 70, two-fifths of women aged 80, and two-thirds of women aged 90. Osteoporosis affects an estimated 75 million people in Europe, USA and Japan. For the year 2000, there were an estimated 9 million new osteoporotic fractures, of which 1.6 million were at the hip, 1.7 million were at the forearm and 1.4 million were clinical vertebral fractures. Europe and the Americas accounted for 51% of all these fractures, while most of the remainder occurred in the Western Pacific region and Southeast Asia. Worldwide, 1 in 3 women over age 50 will experience osteoporotic fractures, as will 1 in 5 men over age 50.

Modern spine surgical techniques encounter difficulty in achieving and maintaining fixation in osteoporotic vertebrae in the case of fracture and/or deformity. The bone-screw interface is typically the region most susceptible to loosening and failure. Many physical factors may affect the final fixation strength of pedicle screws such as screw pitch and diameter, yet host factors have at least as much effect. Pedicle screws have been shown to loosen in patients with compromised bone strength arising from renal osteodystrophy and osteoporosis. A significant portion of these cases will sustain catastrophic failure after attempted surgical fixation. As a result, some spine surgeons may refuse to perform stabilization surgery on osteoporotic patients with fractures and/or severe deformities. There have been many attempts to improve the holding capacity of pedicle screw constructs in osteoporotic bone including the addition of various cements for augmentation and the use of novel screw designs such as expandable screws. Use of polymethylmethacrylate (PMMA) cement has been shown to increase pull-out strength up to 150%. Use of cement to augment traditional pedicle screw fixation generally yields increased resistance to pullout and/or toggle failure in the cephalad-caudad direction as reported in numerous studies, but there are associated potential morbidities such as spinal canal extrusion or vascular flow obstruction.

A further and significant disadvantage of the use of PMMA screw augmentation is that it is a non-biological repair that make revision or re-operation very difficult. It is a "bridge burning" procedure.

Similar problems of initial fixation strength and subsequent loosening and failure exist with the use of screws in orthopedic procedures such as hip fractures that often occur in patients with osteoporotic or otherwise compromised bone.

Moreover, there is a desire for implants to bond effectively and rapidly to surrounding bone, particularly when that bone is compromised. Various strategies are employed to facilitate this including the use of porous ingrowth surfaces. Implant loosening however remains a problem and concern to orthopedists.

When tendon or ligament tissues or grafts are placed either in apposition to bone, as in the case of rotator cuff repair or in bone tunnels as in anterior cruciate ligament repair, the creation or recreation of the tendon-bone enthesis is a problem and concern to orthopedists.

SUMMARY OF INVENTION

The inventors have advantageously discovered a composition and method of improving the fixation of implants and tissue to bone through the use of an implant, which may, for example, be composed of a plurality of fibers of demineralized bone (i.e., demineralized bone fibers (DBF), collagen fibers, synthetic polymers, resorbable fibers) and formed into an appropriate shape. The implant according to some embodiments of the present invention may be placed at i) the interface between the tissue and bone, or ii) may be placed in a hole of a bone prior to insertion of a screw.

In some embodiments of the present invention, a composition and method are provided for improving the fixation of screws in bone using a fiber implant as disclosed herein. For example, the fiber implant may be composed of a plurality of fibers that are formed into an appropriate shape. Using the implant, kits, and/or methods as disclosed herein, the implant is placed in the hole in the bone to be repaired. More specifically, the implant is placed in the hole of the bone in which a bone screw it to be placed. By placing the implant in the hole of the bone prior to the insertion of the screw, the implant contacts the implant and provides a denser substance into which the screw may be secured, thereby increasing the insertion torque and the force required to pull the screw back out of the hole. As such, the implant provided in the hole of a bone prior to insertion of a bone screw decreases the chances of the screw being able to dislodge from the hole and allows for a more secure and effective bone repair. For example, as demineralized bone fibers (DBF) are both osteoinductive and osteoconductive, there is an additional benefit of an DBF fiber implant providing an increase in the local bone growth around the implant and further increasing the likelihood of a long term and possibly permanent bone repair. Additionally, other fiber forms (e.g., collagen fibers, biocompatible polymer fibers, and/or resorbable polymer fibers) may also be osteoinductive and/or osteoconductive. The benefits of these fiber implants are of particular relevance when the screw is being implanted into osteoporotic bone or into an existing screw hole, as in the case of revision surgery.

Notably, the inventive subject matter includes an implant for bone repair or screw fixation, wherein the implant includes a plurality of fibers forming a shape of a cylinder, a tube, a cannulated cylinder, a truncated cone, a cannulated truncated cone, a truncated cone with a flared end, or a cannulated truncated cone with a flared end, tube with a flared end, or a truncated cone shape. In preferred embodiments, the plurality of fibers are cut from demineralized cortical bone. Further, the implant has a proximal end and a distal end. For screw fixation, preferably, the plurality of fibers form the shape of a truncated cone with a flared end, a tube with a flared end, or a cannulated truncated cone with a flared end, and the flared end is at the proximal end of the implant. The length of the implant may be of between 1 cm and 10 cm. Preferably, the length of the implant is 4 to 5 cm. More preferably, the implant has a length of 4 cm. The volume of the implant having a length of between 1 and 10 cm, may also have a volume of between 0.15 $cm^3$ to 10.0 $cm^3$. More preferably, the volume of the implant may be of between 0.15 $cm^3$ to 2 $cm^3$.

Typically, the flared end of the implant has an indent for receiving a bone screw.

In other typical embodiments, the implant is dehydrated.

The inventive subject matter also includes methods of augmenting fixation of a screw in a bone with the implant disclosed above and herein, in which optionally a guide wire may be placed to define a position in the bone for the screw, followed by inserting or providing the implant to a cavity in the bone, and then inserting or providing the screw into the implant.

Specifically, when the guide wire is used, the method includes placing the implant on the guide wire through the cannulated, tubular, or cone shape of the implant and moving the implant along the guide wire into the cavity, facilitating placement of the implant and also preventing or decreasing the incidence of the implant buckling. For moving the implant along the guide wire, a custom pusher, an awl, a tap, and/or a drill may be used. Additionally, the cavity in the bone may be formed using an awl, a tap, and/or a drill. The formation of the cavity using the awl or tap reduces the incidence of any removal of the bone and inducing compaction to reinforce fixation of the screw in the bone. The cavity in the bone may be provided with additional demineralized bone fibers (DBF), biocompatible polymer fibers, collagen fibers, and/or resorbable polymer fibers.

In preferred embodiments, the method of augmenting fixation of a screw in a bone with one of the presently disclosed implants includes placing a guide wire to define a position in the bone for the screw, thereby decreasing the incidence of buckling of the implant, inserting or providing the implant to a cavity in the bone, and inserting or providing the screw into the implant wherein the inserting or providing of the implant or the screw includes using a cannulated instrument or an open-ended syringe with the implant contained therein. The implant may be made of demineralized bone fibers (DBF), biocompatible polymer fibers, collagen fibers, and/or resorbable polymer fibers, and the implant may be provided with additional fibers of the same or different type as disclosed herein. The implant made of the DBF fibers may be both osteoinductive and osteoconductive.

The inventive subject matter also includes methods of fabricating the fiber implant. A method of fabricating the presently disclosed fiber implant includes dispersing a plurality of fibers (D3F, biocompatible polymer fibers, collagen fibers, and/or resorbable polymer fibers) in a fluid, wherein the fibers and the fluid are in a ratio of between about 1 gram of fibers to about 3 mls to about 50 mls of the fluid, providing the dispersed plurality of fibers with pressure into a vented mold thereby draining the fluid out of the mold. Preferably, the fibers and the fluid are in a ratio of 1 gram of fibers in about 3 mls to 20 mls of fluid. More preferably, the fibers and the fluid are in a ratio of 1 gram of fibers in about 3 mls to 10 mls of fluid.

In additional embodiments, the method disclosed above and herein also includes heating the plurality of fibers in the mold. Preferably, the heating occurs at or between about 35 to 55 degrees Celsius. In some embodiments, the method also includes lyophilizing the plurality of fibers.

The inventors have also contemplated a kit for augmenting fixation of a screw in a bone, wherein the kit includes at least one of the presently disclosed fiber implants as disclosed above and herein. The contemplated kit may also include a guide wire, an awl or a tap, and/or a screw to be place in the bone to be repaired. In some embodiments, the guide wire, the awl, and/or the tap are disposable.

In addition to screw fixation, the inventors of the presently disclosed subject matter have discovered an advantageous implant for the surgical reattachment of tendon to bone. The presently disclosed implant is at once capable of: 1) providing an osteoinductive and osteoconductive implant to facilitate regeneration of the enthesis, 2) augmenting the effectiveness of the suture anchor, and 3) self-stabilizing during surgery unlike other implants. Accordingly, aspects of embodiments of the present invention are directed to a means of improving the fixation of implants and tissue to bone through the use of an implant, which may, for example, be composed of fibers of demineralized bone, collagen, polymer, and/or resorbable polymer fibers, and formed into an appropriate shape. In particular, the implant made of a plurality of fibers has a peg portion and a sheet portion. According to some embodiments of the present invention a suture anchor may be placed into the peg portion of the implant and the suture anchor driver is then used to hold the implant and suture anchor to allow the combination to be introduced into the joint being treated. By placing the peg portion of the implant into the cavity placed to receive the suture anchor and screwing the suture anchor into place, the sheet portion of the implant is held in the desired place on the bone bed where the tendon is being reattached. In this way, the sutures can be used to reapproximate and tie down the tendon to effect repair. For larger repairs multiple implants may be used.

In some embodiments of the present invention, the implant is placed at the interface between a torn rotator cuff tissue and the bone. The implant according to some embodiments of the present invention serves to improve the integration between the tendon and bone and facilitate recreation of the enthesis.

Typical embodiments of the present invention include an implant for tendon-to-bone reattachment, the implant made of a plurality of fibers cut from demineralized bone, the plurality of fibers forming a contiguous shape having a peg portion and a sheet portion. In particular, the peg portion has a tubular shape with a closed end and an open end and is capable of being inserted closed-end first into a cavity of a bone. The sheet portion has two sides, and a first side is in contact with an area on the surface of the bone adjacent the cavity. In typical embodiments, the second side of the sheet portion contacts the tendon and the sheet portion thereby forms an interface between the tendon and the bone.

In specific embodiments, the length of the peg portion of the implant is of between about 10 to 50 millimeters (mm). The diameter of the peg portion may be of between about 3 to 10 mm.

In other specific embodiments, the sheet portion of the implant may be any shape so long as it fans out on the surface of the bone and surrounds the open end of the cavity. For example, the overall sheet portion surrounding the region of the peg portion may be in a shape of or similar to a rectangular, a square, a circle, or a non-perfect shape thereof and having a perimeter that forms a rectangle, a square, a circle, or an irregular shape thereof. Additionally, the sheet portion may not form a particular polygon shape, but has a perimeter of straight sides. The straight sides may each independently have a length of between 5 and 20 mm. In example embodiments, in which the sheet portion has a circular shape, the diameter of the circular shape may be of between about 5 and 20 mm. In additional or alternative embodiments, the sheet portion may have a thickness of between about 0.5 to 5 mm.

The implant made of a plurality of fibers as described herein having a peg portion and a sheet portion, may be made of demineralized bone fibers (DBF), collagen, polymer, and/or resorbable polymer fibers. Preferably, the implant is made of a plurality of DBF fibers.

The inventive subject matter also includes a method of augmenting reattachment of a tendon to a bone using the implant as disclosed herein. The method includes placing a suture anchor into the peg portion of the implant, optionally preparing a bleeding bone bed on the bone, creating a cavity in the bone, placing the peg portion of the implant into the cavity in the bone, screwing the suture anchor into place, and using the sutures to re-approximate and tie down the tendon to effect the reattachment of the tendon to bone.

The inventive subject matter also includes a method for making the presently disclosed implant. In typical embodiments, the method for making the presently disclosed implant includes dispersing a plurality of fibers with pressure (under pressure) into a vented mold thereby draining the fluid from the mold. The method may further include heating the plurality of fibers in the mold. Heating of the plurality of fibers may occur at or between 35° to 55° or 45° to 55° C. In example embodiments, the fibers (e.g., demineralized bone fibers) are lyophilized.

The inventors also contemplated methods of augmenting a tendon to bone reattachment procedure in which the implant as disclosed herein is placed between the tendon and the bone.

Additional embodiments of the contemplated subject matter include a method of facilitating the surgical placement of an orthopedic bone implant wherein the method includes augmenting the orthopedic bone implant with a peg portion. The orthopedic bone implant may be an existing sheet implant known in the art. As such, methods may include modifying the sheet form or modifying the manufacture protocol of the sheet form to include a peg portion attached thereto.

Aspects of the inventive subject matter include an augmented implant wherein an implant (e.g., a sheet implant) is modified to have a stabilizing portion. The stabilizing portion may increase the effectiveness of sutures used to place the implant for the needed surgical repair. Furthermore, the stabilizing portion may increase the stability of the implant while the implant is being surgically placed and/or tethered into place. For example, the stabilizing portion may be a peg portion. The peg portion may be solid or tubular (e.g., hollow) with an open and closed end.

BRIEF DESCRIPTION OF THE DRAWINGS

The patent or application file contains at least one drawing executed in color. Copies of this patent or patent application publication with color drawings will be provided by the Office upon request and payment of the necessary fee.

FIG. 8 shows a sheet mold 17 and sheet 18 produced from it. The thickness and density of the sheet are controlled by varying the quantity of DBF used and the spacing between the lid and the bottom of the mold, according to some embodiments of the present invention.

In FIG. 20a a guide wire 47 is placed in the bone.

In FIG. 20b a cannulated awl 48 is placed over the guide wire. In FIGS. 20c and 20d, the awl is shown being pushed and turned into the bone to form a cavity 49 as shown in FIG. 20e.

In FIG. 21a the implant 50 is shown being placed on the guide wire 47. In FIGS. 21b and 21c the implant can be seen being pushed into the cavity 49. FIG. 21d shows a cannulated pedicle screw 51 with a cannulated driver 52 placed over the guide wire and used to push the implant 50 into the cavity. FIG. 21e shows an alternative method where the awl 48 is used as the pusher. FIGS. 21f and 21g show the screw being inserted into the bone. When the screw is fully inserted the driver 52 and guide wire 47 are removed as is shown in FIG. 21h. While not part of the procedure for the purposes of illustration in FIG. 21i the screw has been removed allowing the placement of the implant 50 to be seen.

FIGS. 25a-25e shows a device for use in acl augmentation. In FIG. 25a the components 59 of the device are two sheets of DBF. FIG. 25b shows them slotted together to make a cruciate form 60.

FIG. 25c shows the four strands 61 of a hamstring graft positioned within the cruciate device 60. Whipstitching the graft in preparation for implantation serves to cause the sheet to conform around the outside of the graft as shown in FIG. 25d and hold it in place. One device is placed at each end of the graft as is shown in FIG. 25e.

FIG. 26 shows a device for use in acl augmentation. In FIG. 26a the components 59 of the device that are two sheets of DBF, one wider than the other. FIG. 26b shows them slotted together to make a cruciate form 60. FIG. 26c shows the four strands 61 of a hamstring graft positioned within the cruciate device 60. Whipstitching the graft in preparation for implantation serves to cause the sheet to conform around the outside of the graft as is shown in FIG. 25d and hold it in place. One device is placed at each end of the graft as is shown in FIG. 26e.

FIG. 27a shows a variant of the device fabricated from two DBF sheets 62 and 63 that are shaped to wrap around the tendon (not shown). FIG. 27b is a photograph of a device fabricated from a DBF sheet and FIG. 27c is a variant using a single DBF sheet that can be used with a two strand graft.

In FIG. 30b a dilator 72 is shown that is intended to create a defect in bone to receive the device 68. The dilator has a depth mark 73 that indicates the depth of hole to be made. FIG. 30c shows a suture anchor 25b mounted on the driver 74 used to implant it. In FIG. 30d the suture anchor has been introduced into the cavity 70 in the device. Note that the suture anchor 25b cannot be seen in the FIG. due to the device.

DETAILED DESCRIPTION

Figure 1:
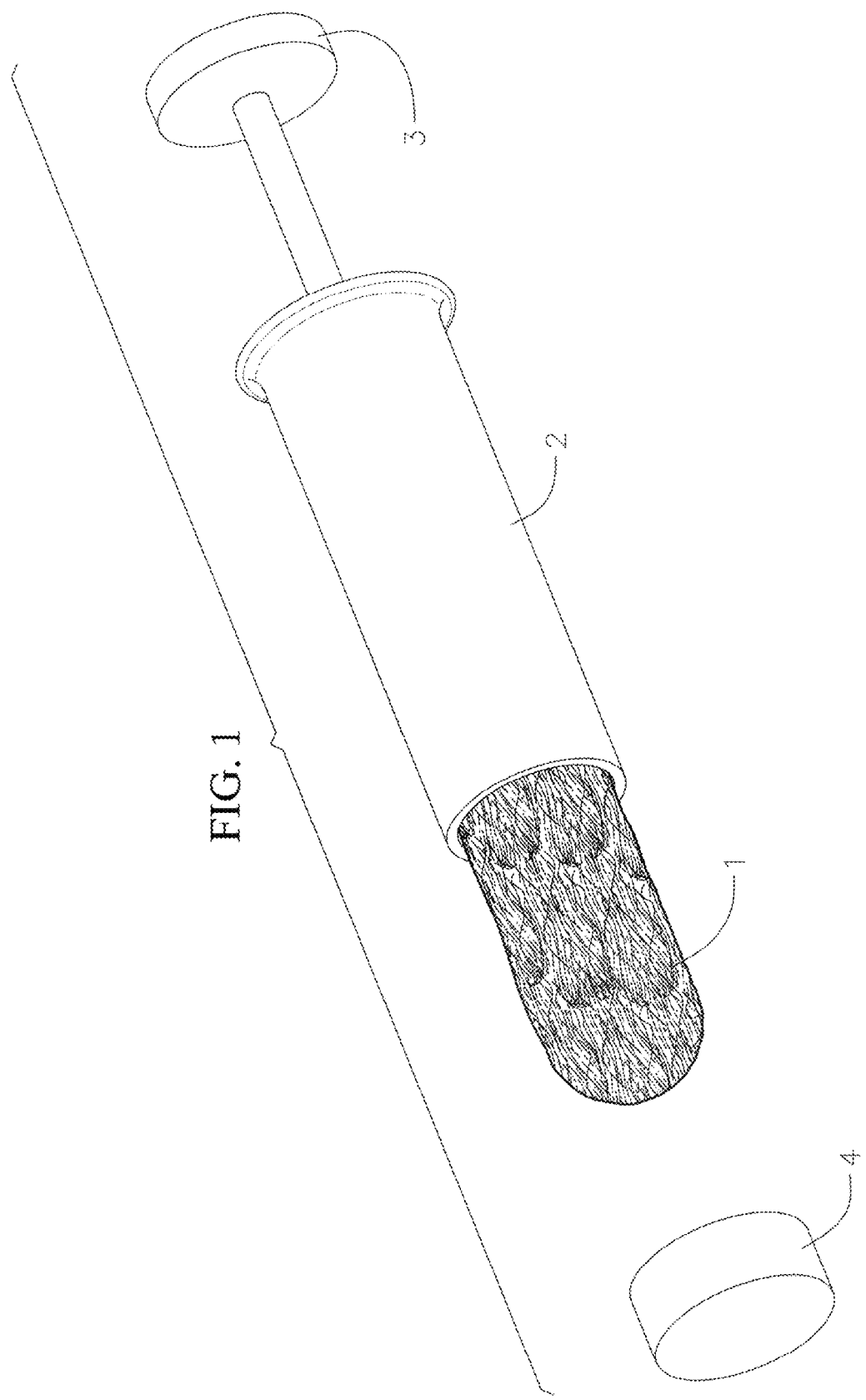
FIG. 1 shows an implant for augmentation of screw fixation and delivery device, according to embodiments of the present invention where the implant 1 is placed in the tubular portion of the delivery instrument 2 and is expelled from the device using the plunger 3 where an optional protective cap 4 may be included and is removed prior to use.

Aspects of the embodiments of the present invention are directed to an approach for augmenting bone repair and healing using demineralized bone fiber (DBF), collagen, polymer, and/or resorbable polymer fiber implants.

In some aspects, embodiments of the present invention include fiber implants, methods of forming fiber implants, and kits including suitably shaped and sized cylindrical fiber implants for augmenting the fixation of screws in osteoporotic or otherwise compromised bone. This approach includes a cylinder of demineralized bone fibers (DBFm) that may be inserted into a hole in a bone in need of repair for the implant to be placed together with and prior to the placement of a bone screw. The cylinder is sized to be the same diameter as the screw hole. At the time of surgery, the presence of the device increases the torque required to insert the screw and increases the pull out force that would be required to displace the screw. The additional benefit of using the DBF material is that it is osteoinductive and will cause an increase in local bone formation around the screw providing long term enhancement of fixation. The DBF implant is placed into the hole of the bone prior to insertion of the screw.

In other aspects, embodiments of the present invention include DBF, collagen, polymer, and/or resorbable polymer fiber implants, and methods forming DBF, collagen, polymer, and/or resorbable polymer fibers implants, and kits including suitably formed DBF, collagen, polymer, and/or resorbable polymer fiber implants for use as an interface between the bone and the ligament or tendon to be repaired. For example, a sheet of DBF may be used in the bone tunnels of a soft tissue ligament replacement such as an acl (anterior cruciate ligament) surgery where a hamstring or tendon autograft is fixed into a bone tunnel. Additionally, a sheet of DBF may also be used in a rotator cuff repair in which the DBF sheet is placed onto the bone bed between the bone and the tendon to be reattached.

As used herein "implant," "fiber implant," "implant of the present disclosure," and like terms are used interchangeably to refer to a suitably shaped fiber implant made using demineralized bone fibers (DBF) as disclosed herein and disclosed in U.S. Pat. Nos. 9,486,557 and 9,572.912, and WO 2016123583, the entire contents of all of which are incorporated herein by reference. For example, as shown throughout the present disclosure, suitably shaped DBF implant includes a sheet of DBF, cylinder-shaped, or truncated cone forms of DBF.

Additionally, for collagen, polymer, and/or resorbable polymer fiber implants are made following the methods disclosed herein for DBF with a substitution or addition of the collagen, polymer, and/or resorbable polymer fibers. While DBF fibers are exemplified herein, these other fiber forms may also be used to form the presently disclosed fiber implants.

Resorbable polymers are biocompatible polymers capable of resorbing in the body and have a physical strength to form a fiber or particle at room temperature. Non-limiting examples of resorbable polymers include silk, collagen (including Types I to V and mixtures thereof), and proteins comprising one or more of the following amino acids: alanine, arginine, asparagine, aspartic acid, cysteine, glutamine, glutamic acid, glycine, histidine, isoleucine, lysine, methionine, phenylalanine, proline, serine, threonine, tryptophan, tyrosine and valine; polysaccharides, including alginate, amylose, carboxymethylcellulose, cellulose, chitin, chitosan, cyclodextrin, dextran, dextrin, gelatin, gellan, glucan, hemicellulose, hyaluronic acid, derivatized hyaluronic acid, oxidized cellulose, pectin, pullulan, sepharose, xanthan and xylan; resorbable polyesters, including resorbable polyesters made from hydroxy acids (including resorbable polyesters like poly(lactides), poly(glycolides), poly(lactide-co-glycolides), poly(lactic acid), poly(glycolic acid), poly (lactic acid-co-glycolic acid), poly(dioxanones), polycaprolactones and polyesters with one or more of the following monomeric units: glycolic, lactic; trimethylene carbonate, p-dioxanone, or ε-caprolactone, and resorbable polyesters made from diols and diacids; polycarbonates; tyrosine polycarbonates; polyamides (including synthetic and natural polyamides, polypeptides, and poly(amino acids)); polyesteramides; poly(alkylene alkylates); polyethers (such as polyethylene glycol, PEG, and polyethylene oxide, PEO): polyvinyl pyrrolidones or PVP; polyurethanes; polyetheresters; polyacetals; polycyanoacrylates; poly(oxyethylene)/poly(oxypropylene) copolymers; polyacetals, polyketals; polyphosphates; (phosphorous-containing) polymers; polyphosphoesters; polyalkylene oxalates; polyalkylene succinates; poly(maleic acids); biocompatible copolymers (including block copolymers or random copolymers); and hydrophilic or water soluble polymers, such as polyethylene glycol, (PEG) or polyvinyl pyrrolidone (PVP), with blocks of other biocompatible or biodegradable polymers, for example, poly(lactide), poly(lactide-co-glycolide), or polycaprolactone or combinations thereof. Resorbable polymers also include cross-linked polymers, and include, for example, cross-linked collagen, as well as functionalized polymers. In some embodiments, resorbable polymers are resorbable polyesters.

In further embodiments, the DBM, synthetic polymer, collagen, or resorbable polymer fibers may be coated (e.g., at least in part) with a calcium ion donor compound. Examples of calcium ion donor compounds include calcium peroxide, calcium ascorbate, calcium sulfate, calcium phosphate, calcium carbonate, calcium chloride, and mixtures thereof.

The popularity of demineralized bone matrix (DBM)-based products is based on the ability to induce bone formation through expression of inherent non-collagenous proteins that stimulate some cell types present at the graft site to differentiate into bone forming cells. This induction of bone formation process is referred to as "osteoinduction" and is due to the natural presence of bone morphogenic proteins (BMPs). DBM also provides a scaffold for these cells to populate and spread throughout in a process known as "osteoconduction." Demineralized bone in the form of a fiber, known as Demineralized Bone Fiber (DBF) has a physical form that has been shown to optimize and enhance the osteoconductive performance of DBM. In some embodiments of the present invention, a composition and method of manufacture of DBF fibers is as disclosed in U.S. Pat. Nos. 9,486,557 and 9,572,912, supra. When DBM or DBF is combined with osteogenic cells that are capable of forming bone, the three mechanisms of bone healing (e.g., osteoinduction, osteoconduction, and osteogenesis) are combined.

In exemplary embodiments, the DBF implant is dried so that the implant has sufficient rigidity to allow it to be pushed into a pre formed hole. The DBF fibers may be easily formed into any of the required implant shapes using molding or wet laying processes prior to drying. Optionally a heating step may be utilized which has been shown to impart even greater cohesion to formed DBF implants without affecting the implant's osteoinductivity.

Figure 2:
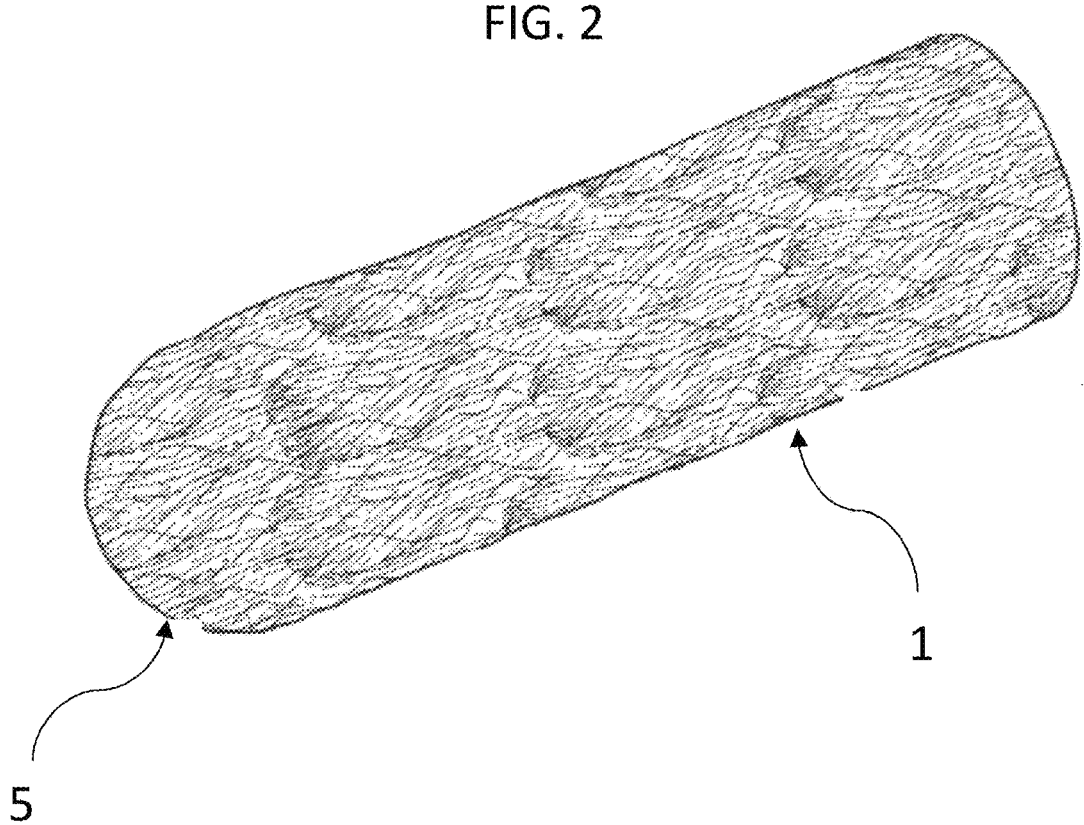
FIG. 2 shows a variant of the implant 1 wherein the front of the cylinder has a domed shape 5 to facilitate insertion, according to some embodiments of the present invention.
Figure 3:
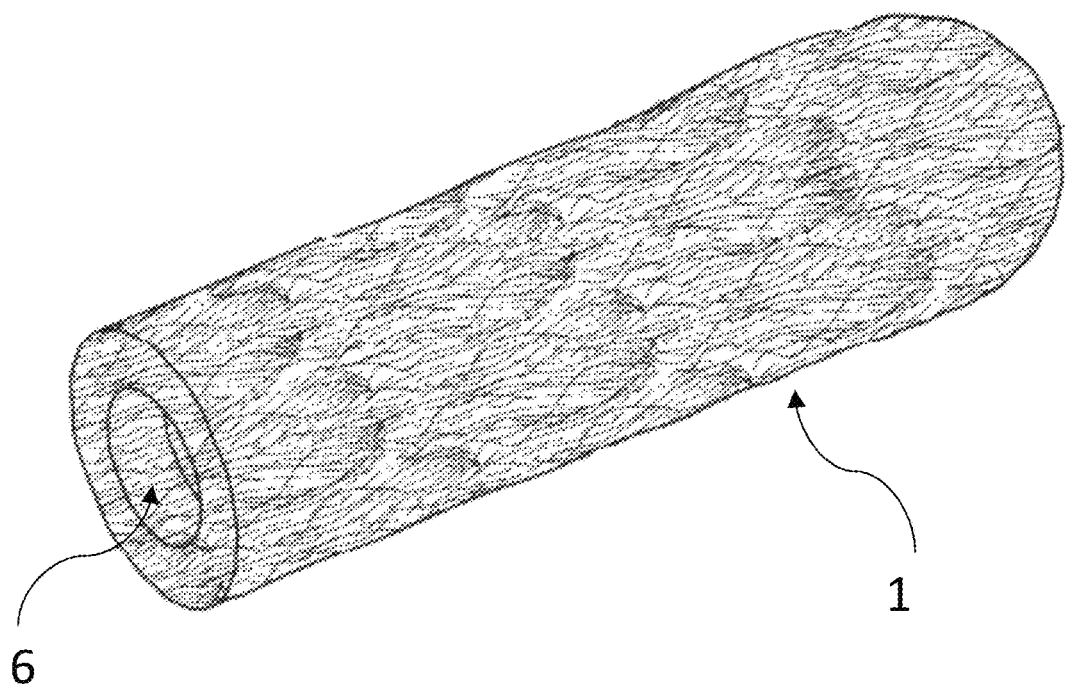
FIG. 3 shows a variant of the implant 1 wherein the rear of the cylinder has a central depression 6 to facilitate insertion of the screw centrally in the implant, according to some embodiments of the present invention.
Figure 13:
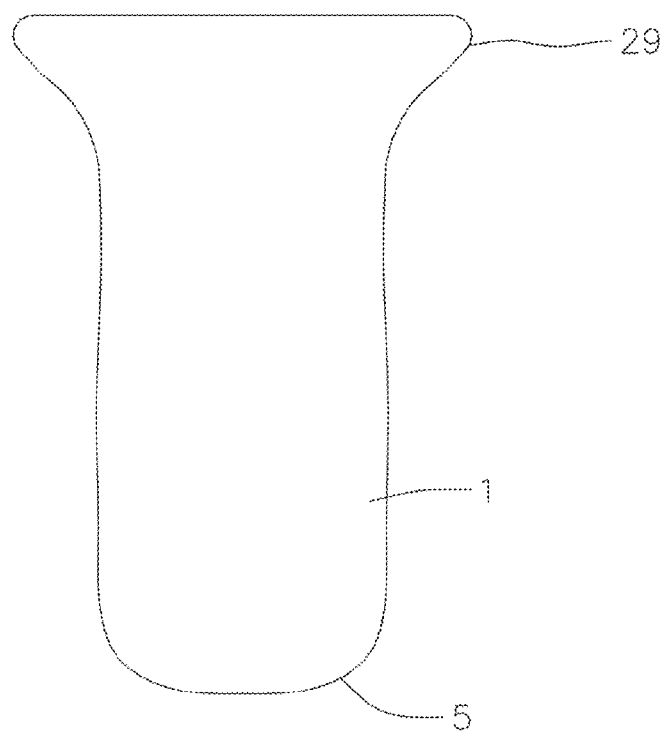
FIG. 13 shows a cross sectional view of a variant of the implant for augmentation of screw fixation 1 wherein in addition to the domed end 5 to aid insertion there is an expanded proximal portion of the implant 29, according to some embodiments of the present invention.

Variations and sophistications to the design include shaping or doming of the distal end of the DBF implant to aid in insertion of the DBF implant into the hole of the bone. An example of such a design is exemplified in DBF implant 5 of FIG. 2. In some embodiments, the proximal end of the DBF implant may also be flared 29 in FIG. 13. This feature may help prevent the implant from being pushed too far into a drilled hole. It will also provide additional DBF fibers at the cortex of the bone and may facilitate healing of that region of the bone. Reformation of the cortex of the bone is particularly important for pedicle screw fixation in spinal surgery as toggling of the screw is the primary mode of loading and hence failure, and the cortex provides the most resistance to this mode of loading.

Figure 14:
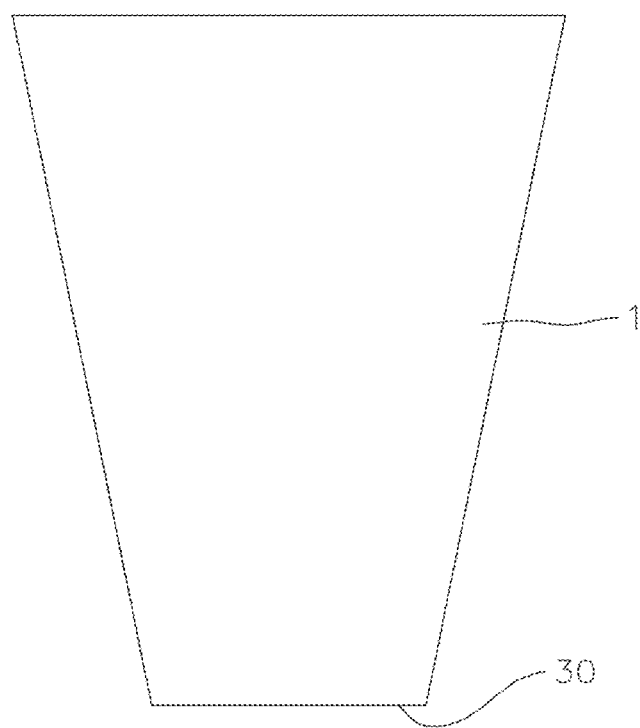
FIG. 14 shows a cross sectional view of a variant of the implant for augmentation of screw fixation 1 wherein the implant is of a narrower diameter at its distal end 30, according to some embodiments of the present invention.

The implant may also be a non-uniform cylinder, i.e. a truncated cone, such that the distal end 30, as shown in the cross-sectional view in FIG. 14 is narrower than the proximal end of the implant. The implant is placed into the hole prior to insertion of the screw.

Figure 15A:
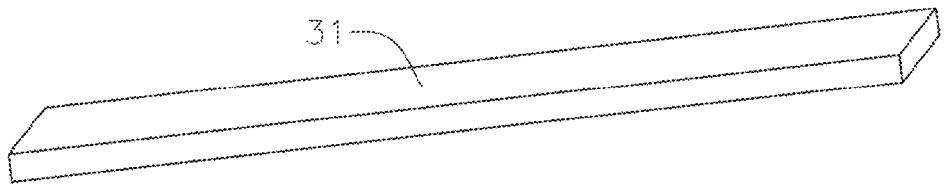
FIG. 15a shows a variant of the implant for augmentation of screw fixation 31 wherein the implant is in the form of a rectangular prism, according to some embodiments of the present invention.

An implant in the shape of a rectangular prism 31 as shown in FIG. 15*a* may also be used for augmentation of screw fixation. The rectangular prisms may be formed individually or may be cut from a sheet of material 18 that has been formed in a mold. A simple rod 36 may be used to aid insertion of the implant into a drill hole. Densification of an area 32 of the implant may be done to provide a strengthened area to aid insertion. An implant 31 in the shape of a rectangular prism with a semi-circular cross section 33 allows for more effective filling of the hole. This can be seen in FIG. 15*h* which is a top view of an implant 31 with a semi-circular cross section 33 placed in a drill hole 35. The implant is placed into the hole prior to insertion of the screw.

In some instances, it will be desired to place an implant in the hole created when a screw is removed from bone, such as in a revision procedure, or in a hole created by an awl. In these cases the distal end of the hole will generally be a smaller diameter than the proximal end. An implant with a shape such as is shown in FIG. 15*d* or 15) is designed to be used in this instance. The implant is placed into the hole prior to insertion of the screw.

While implants according to embodiments of the present invention may be easily placed into drilled holes by hand, it is envisaged that in some instances it may be desired to have the implant that is provided to the surgeon to be pre-loaded into a syringe like device implant shown in FIG. 1. As is shown in this FIG., the implant 1 is held in the body of the syringe 2. In this embodiment, the implant includes a removable cap 4 to maintain the implant in place during storage and transportation, and may optionally have a luer fitting to allow pre hydration of the implant. For implant delivery, the distal end of the syringe is placed over the drill hole and the plunger 3 used to expel the implant. A reusable implant delivery system may also be used.

The hole to receive the implant may be formed by drilling, tapping, or by use of an awl, or may exist through the removal of a screw.

In a variant of an implant according to some embodiments of the present invention, the implant is provided with a hole through its length such that the implant may be delivered over a guide wire.

Figure 22:
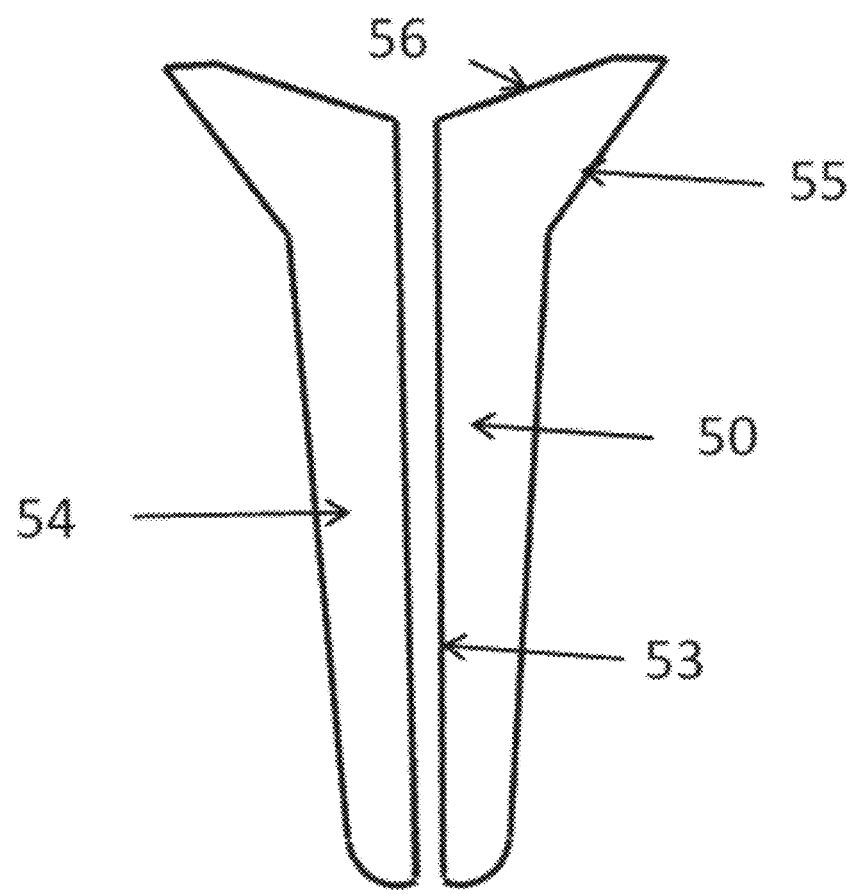
FIG. 22 shows an implant 50 cross section. The implant has a central cannulation 53. The body of the implant 54 is a truncated cone that is narrower at the distal end. A flared top 55 at the proximal end has a depression 56.
Figure 23:
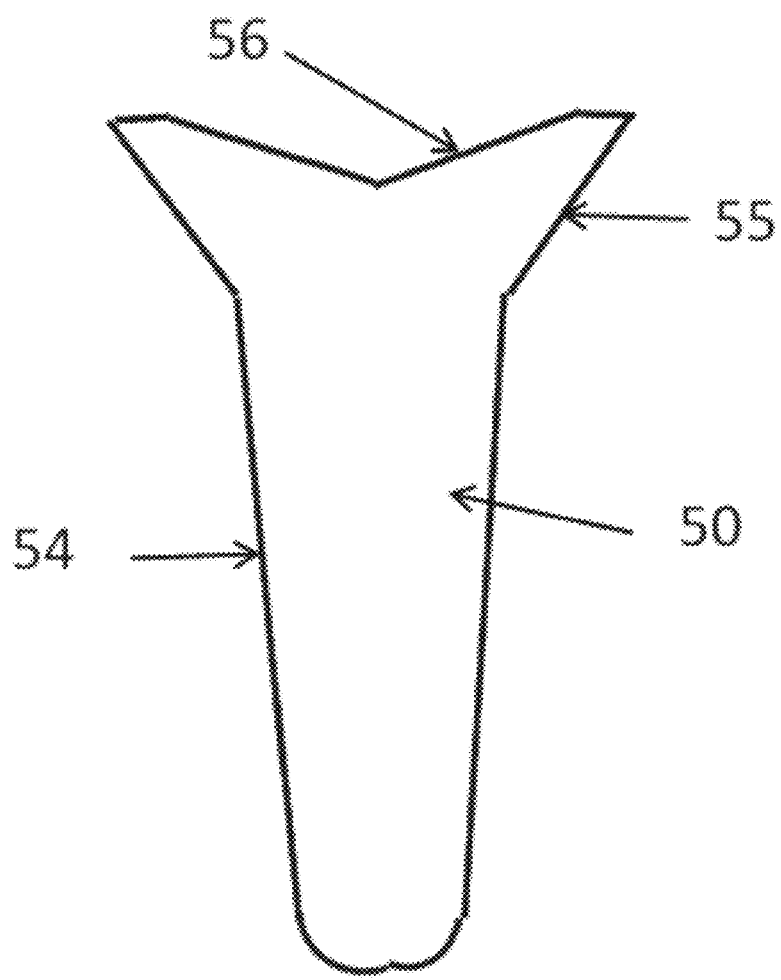
FIG. 23 shows the cross section of a non cannulated implant. The body of the implant 54 is a truncated cone that is narrower at the distal end. A flared top 55 at the proximal end has a depression 56.

When pushing the proximal end of the implant into the hole or cavity in the bone there is a buckling force caused by friction of the implant against the bone. Several factors may be incorporated into the design to accommodate this. Firstly, the implant may be in the form of a truncated cone with the distal end narrower than the proximal end as is shown in FIGS. 22 and 23. Secondly, an awl is used to provide the cavity in the bone that is itself in the overall shape of a truncated cone such that the cavity produced is the same dimensions as the implant. Thirdly an external device may be used to provide support and resistance to buckling on insertion. This may be an open-ended syringe, as disclosed above where the barrel of the syringe provides support to the implant, or it may be by placing the cannulated implant over a guide wire.

It may also be desired to prevent the implant from being displaced too deeply into the bone. In the designs shown in FIGS. 22 and 23 the flared top 53 acts to prevent this occurrence.

The surgical technique for using an implant of this invention is outlined in FIGS. 20 and 21. A synthetic analog of osteoporotic bone 46 produced by Sawbones. Inc. is accepted by the FDA and others as a surrogate for osteoporotic bone. A guide wire 47 is placed in the bone. A shown in FIG. 20*b* a cannulated awl 48 is then placed over the guide wire. The awl is dimensional the same as the implant that is to be used. A further benefit of using an awl is that it does not remove bone tissue, but rather pushes it laterally and forms a densified bone layer that in itself will aid fixation. In FIGS. 20*c* and *d* the awl is shown being pushed and turned into the bone to form a cavity 49 as shown in FIG. 20*e*. The awl is then removed and an implant 50 is selected that corresponds to the size of the awl. Where the implant has a flared end the awl may also have a corresponding feature.

FIG. 21 shows the steps of implant placement and screw insertion. In FIG. 21a the implant 50 is shown being placed on the guide wire 47. In FIGS. 21b and c the implant can be seen being pushed into the cavity 49. FIG. 21d shows a cannulated pedicle screw 51 with a cannulated driver 52 placed over the guide wire and used to push the implant 50 into the cavity. FIG. 21e shows an alternative method where the awl 48 is used as the pusher. FIGS. 21f and g show the screw being inserted into the bone. The guide wire serves an additional purpose in that it helps maintain the screw trajectory in the center of the implant so that DBF is pushed laterally around the whole screw circumference.

Figure 21A:
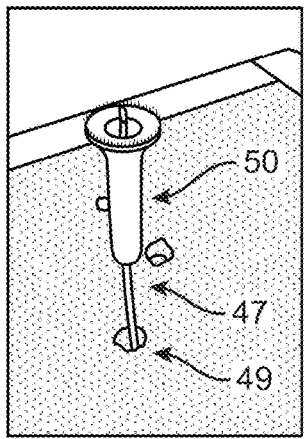
FIGS. 21a-21i show the steps of implant placement and screw insertion.
Figure 21B:
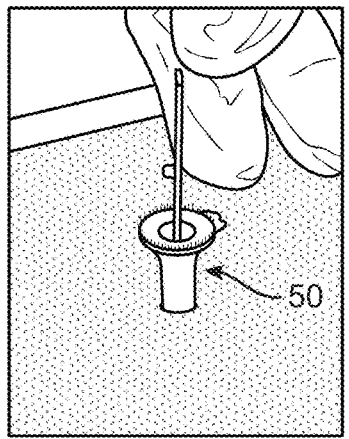
Figure 21C:
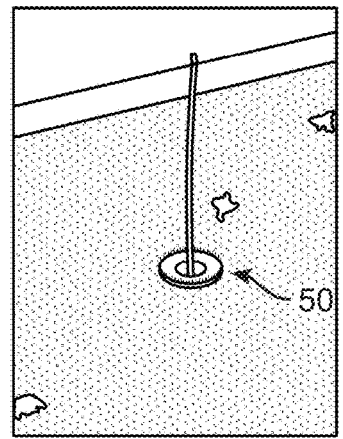
Figure 21D:
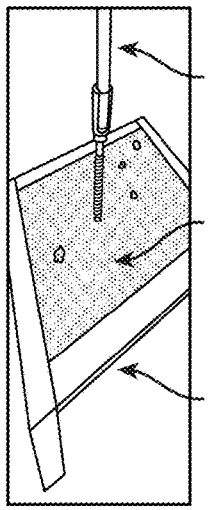
Figure 21E:
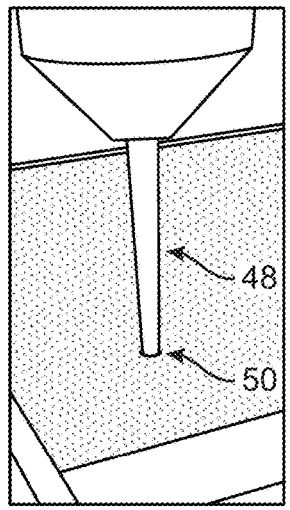
Figure 21F:
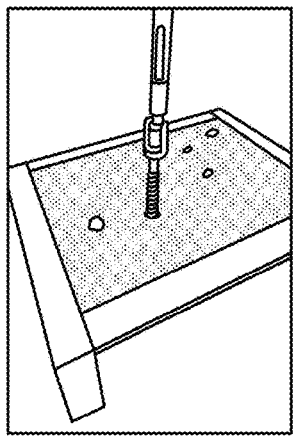
Figure 21G:
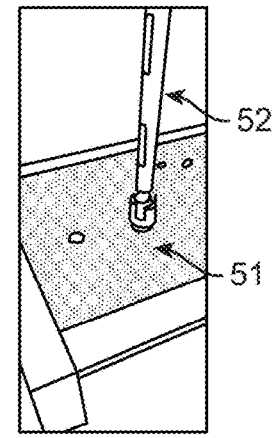
Figure 21H:
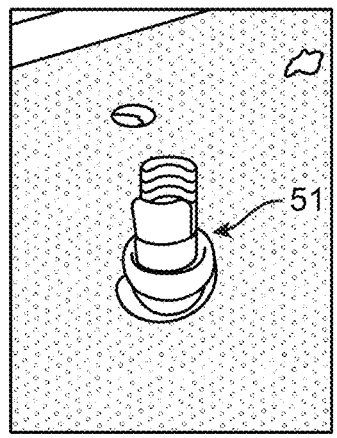

When the screw is fully inserted the driver 52 and guide wire 47 are removed as is shown in FIG. 21h.

Figure 21I:
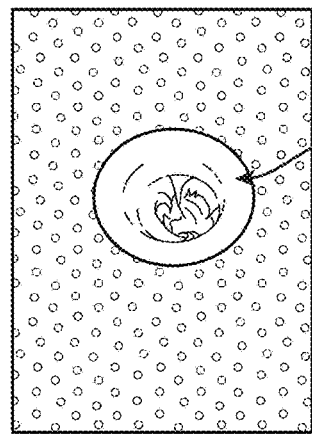

In FIG. 21i the screw has been removed allowing the placement of the implant 50 to be seen. As desired the DBF fibers are displaced laterally by the screw as it is inserted. There is a further advantage of truncated cone and flared end in that it helps to further resist any downward migration of the implant as the screw is inserted.

Another beneficial aspect of the flared design is that a quantity of DBF can be positioned on the surface of the bone. This is the region in for example, the pedicle, where cortical bone is removed to gain access to the pedicle. In use the loading on a pedicle screw tends to "toggle" the screw and loosen it. The primary area of bone that can resist this motion is the cortical surface so the placement of DBF where it can help to stimulate reformation of the cortex is beneficial. If desired the awl could be designed so that the entire flared portion of the implant is positioned on the bone surface.

The implant can be the same length as the screw that it is intended to be used with or it may be shorter.

Where the procedure is desired to be done using a guide wire the device, awl or drill, screw and screwdriver will all be cannulated to accommodate use over a guide wire.

The implant may be supplied as a kit with a guide wire and awl. The kit may also include screws. The guide wire and awl may be supplied as sterile disposable single use items or may be designed to be re-usable.

The implant is dependent on having some rigidity to enable it to be inserted in the bone and as such this is best achieved by using the DBF in a dry state. Once in place in the bone the fibers will hydrate. The effect of this will be to cause them to swell, providing additional fixation.

Figure 18:
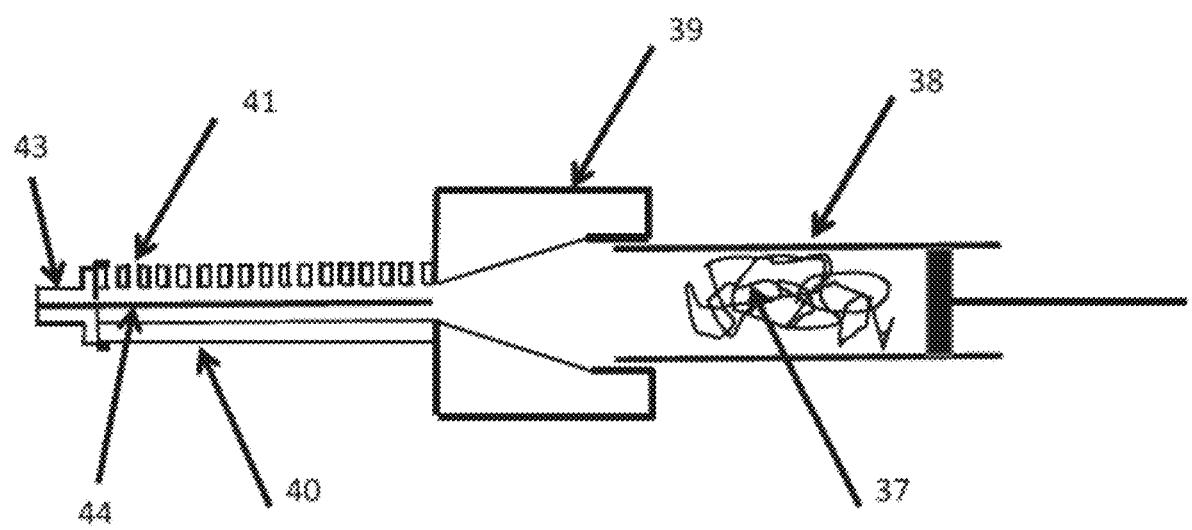
FIG. 18 shows a cross-section view of a variant of the apparatus shown in FIG. 16 that provides for manufacture of a cannulated implant using the water assisted injection molding process. The DBF fibers 37 are loaded into a syringe 38, the distal end of the syringe is fitted into an adapter 39, attached to which is a detachable mold 40, where the mold is tapered towards its distal end and has vents 41 along its length, and a removable vented end cap 43 that also serves to hold a guide wire 44.
Figure 19:
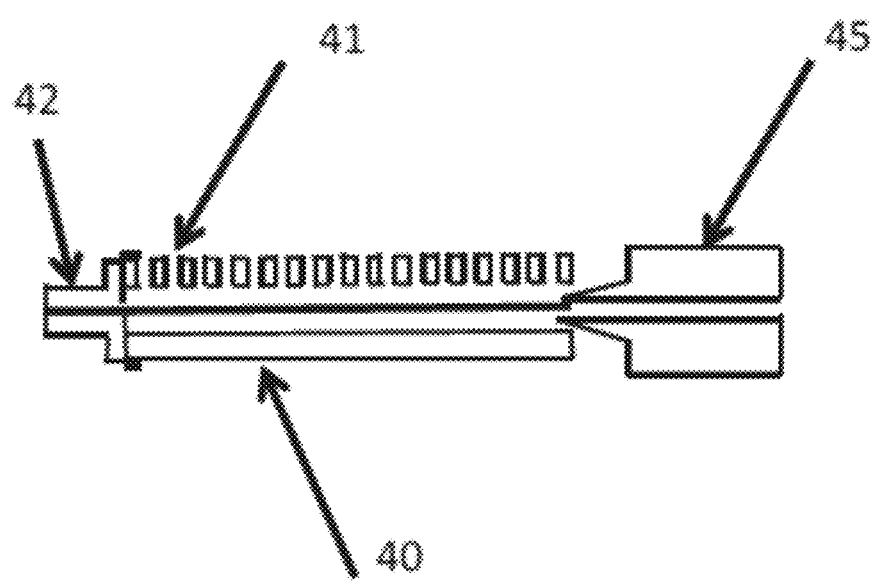
FIG. 19 shows how the detachable mold of FIG. 18 is removed after DBF injection and a cap 45 is placed on the proximal end of the device locating and centralizing the guide wire. The mold is then placed into an oven or lyophilizer for drying, according to some embodiments of the present invention.
Figure 20A:
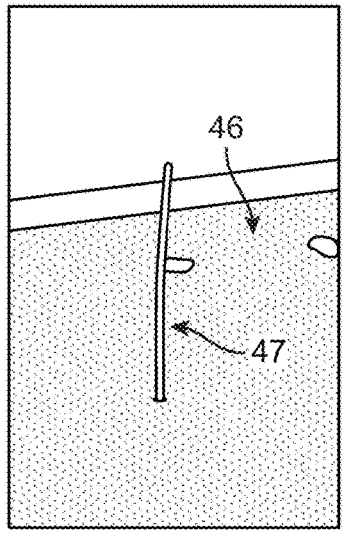
FIGS. 20a-20e show the steps in the surgical implantation technique to create a cavity for implantation of a cannulated implant. For the purpose of the demonstration a synthetic foam analog 46 of osteoporotic bone is used (Sawbones Inc.).
Figure 20B:
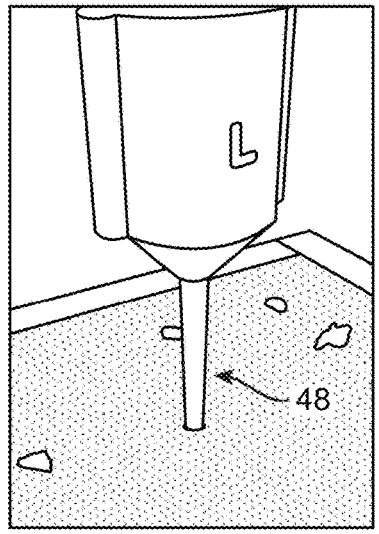
Figure 20C:
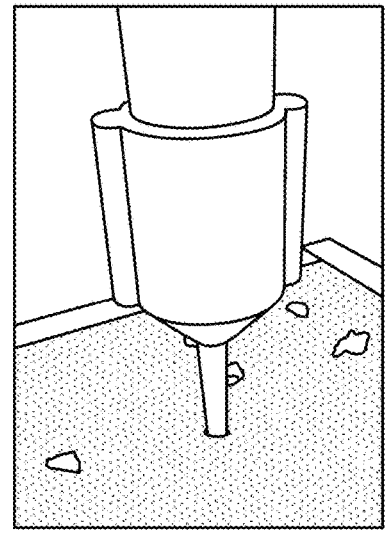
Figure 20D:
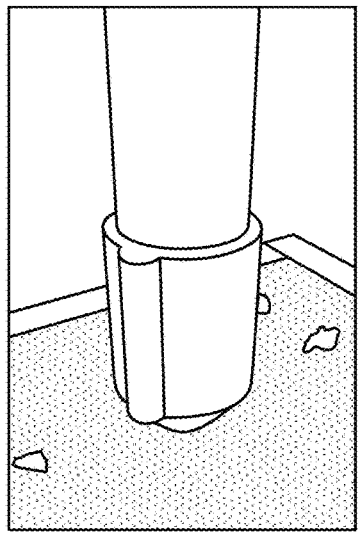
Figure 20E:
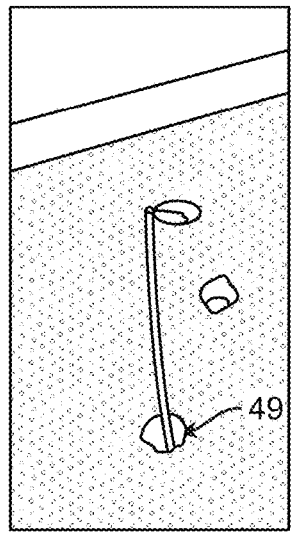
Figure 20F:
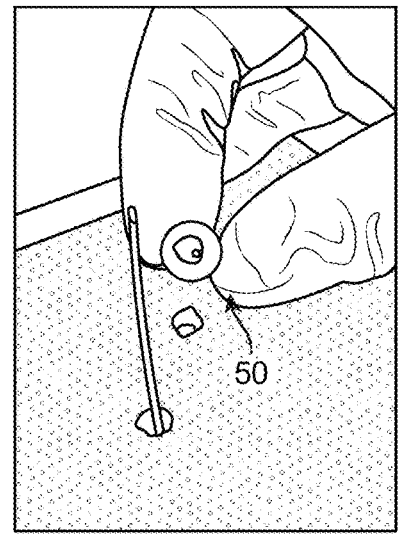
In FIG. 20f, the awl is then removed and an implant 50 is selected that corresponds to the size of the awl.

In other embodiments of the present invention, with reference to FIG. 18, DBF in the form of a thin sheet 18 may also be used to act as an interface between an implant and surrounding bone. The DBF sheet will facilitate conformity of the implant to the surrounding bone and will subsequently, through its osteoinductive nature, stimulate bone formation and integration of the surrounding tissue with the implant.

DBF in the form of a hydrated thin sheet may also be pressed onto the surface of a screw or implant prior to implantation for similar effect.

Figure 10:
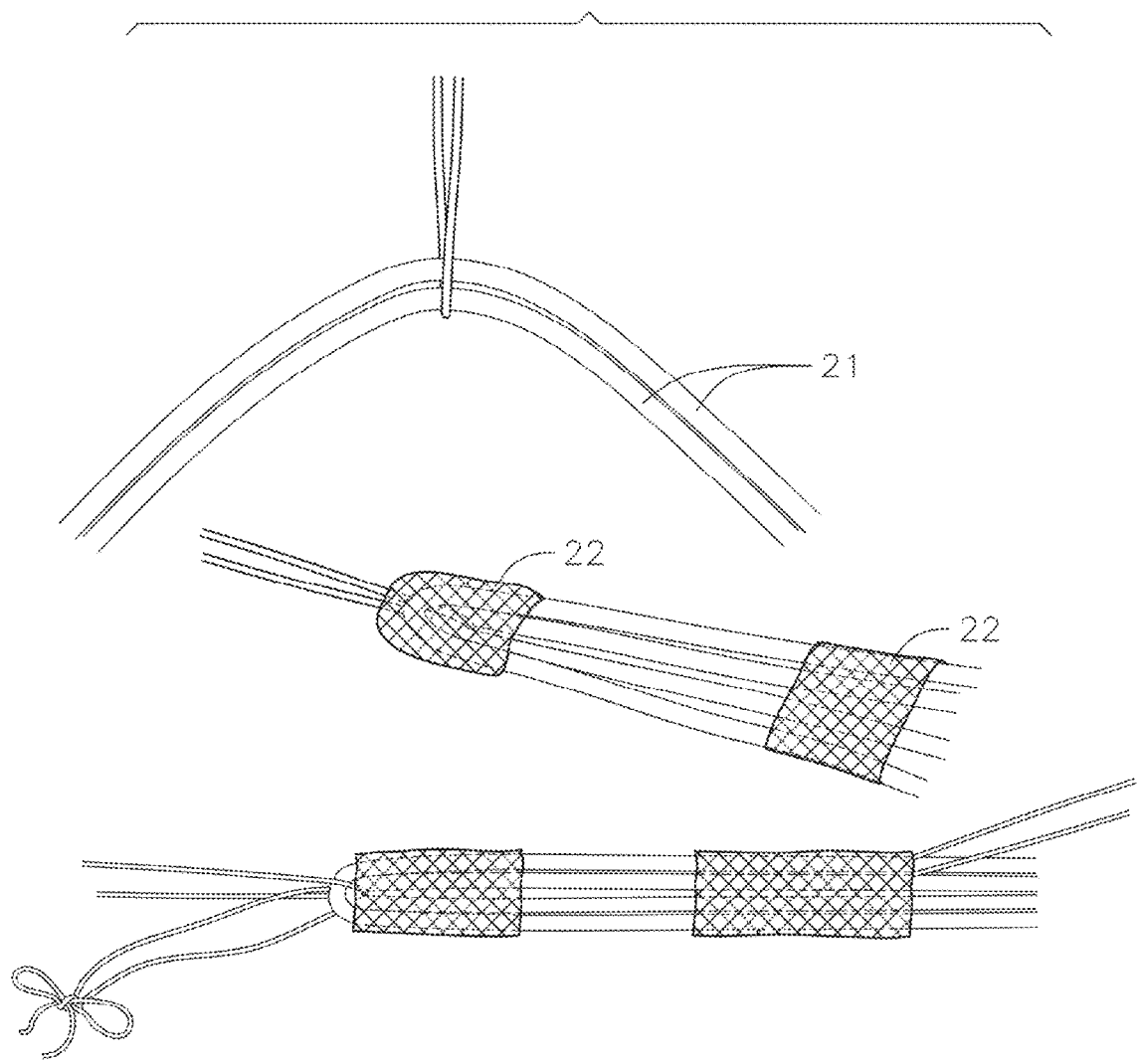
FIG. 10 shows a hamstring graft 21 with a DBF sheet 22 sutured into the regions of the graft destined for the bone tunnels, according to some embodiments of the present invention.

DBF in the form of a thin sheet may also be used to stimulate bone formation in the bone tunnels of a soft tissue ligament replacement such as an acl (anterior cruciate ligament) surgery where a hamstring or tendon autograft is fixed into a bone tunnel. In this usage, as shown in FIG. 10 a sheet of DBF 22 may be sutured onto the hamstring graft 21 prior to implantation into the patient with the DBF positioned so that it is in tunnel portion of the graft, and may optionally be hydrated to aid its conformity. The osteoinductive nature of the DBF material will stimulate bone to graft healing. The sheet may be simply wrapped around the outside of the hamstring or tendon bundle or may be incorporated in a way that provides DBF between the individual tendons. Suture may be used to hold the DBF sheet in place and may be whipstitched in place during the existing graft preparation step.

It is desired to stimulate bone formation throughout the graft within the bone tunnel as well as stimulate the formation of the tendon bone interface. To this end it is desirable to have D3F within the strands of the graft. One means of achieving this is to use two pieces of the DBF sheet and place slots in them so that they can be slotted together to form a cruciate shape. Examples of how this could be done are shown in FIGS. 25, 26 and 27. While the most common graft uses four strands the design in FIG. 27c shows how simply the design can be adapted for a two strand graft by using a single sheet of DBF.

Figure 28A:
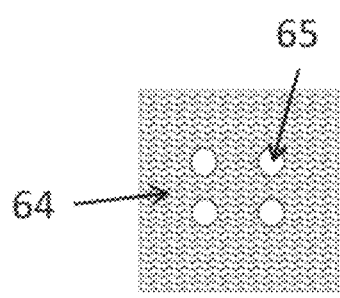
FIG. 28a shows a device for acl augmentation fabricated from a DBF sheet 64 that has four holes 65.
Figure 28B:
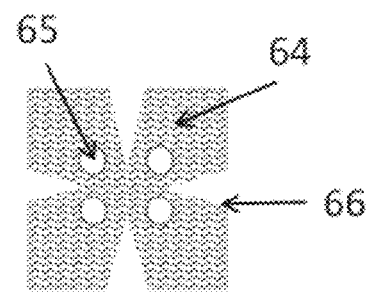
FIG. 28b shows a device for acl augmentation fabricated from a DBF sheet 64 that has four holes 65 and four cut outs 66. The four strands 61 of the graft are threaded through the holes prior to whipstitching to provide the graft ready for implantation in FIG. 28c.
Figure 28C:
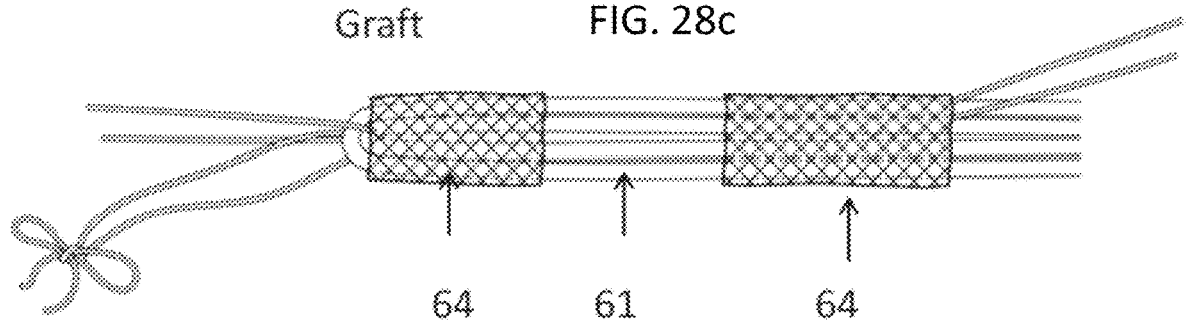

An alternative format of the device is to use a sheet of DBF and cut or punch holes in it that the strands of the graft can be threaded though as is shown in FIG. 28a and FIG. 28b.

Figure 11:
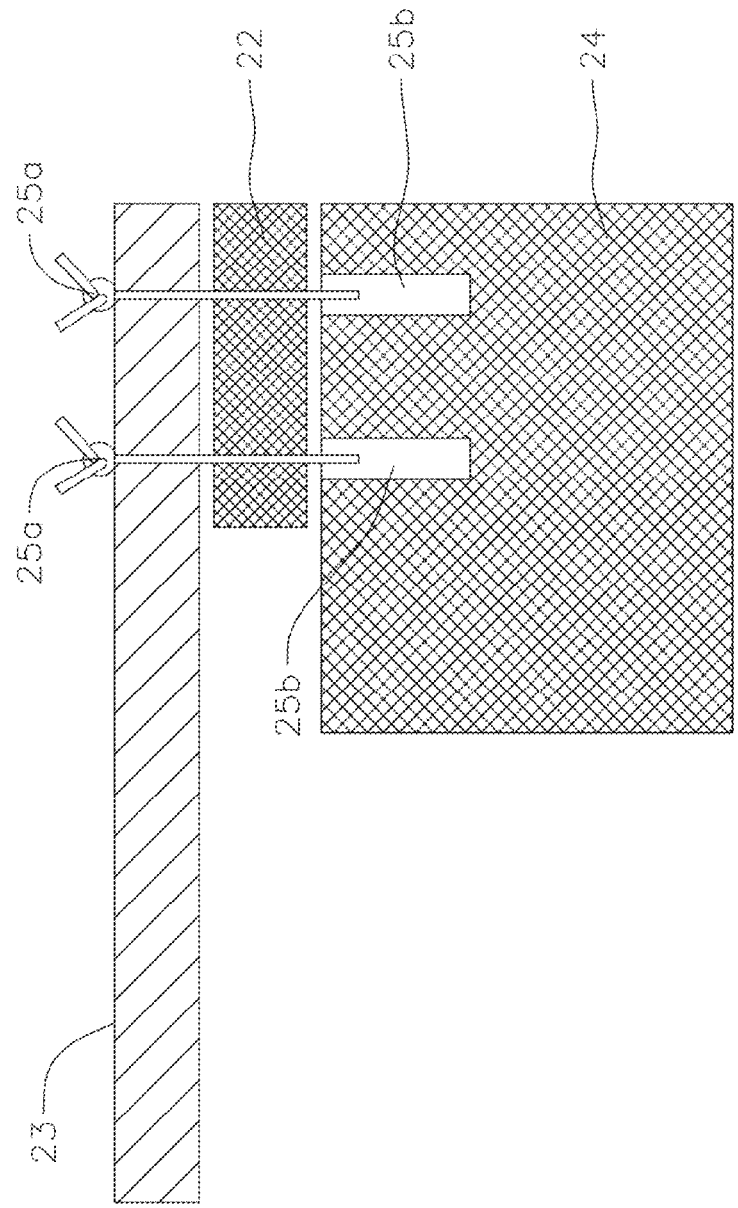
FIG. 11 shows a sheet of DBF 22 placed between the tendon 23 and bone 24. Also shown are sutures 25a and suture anchors 25b used to reattach the tendon, according to some embodiments of the present invention.
Figure 12:
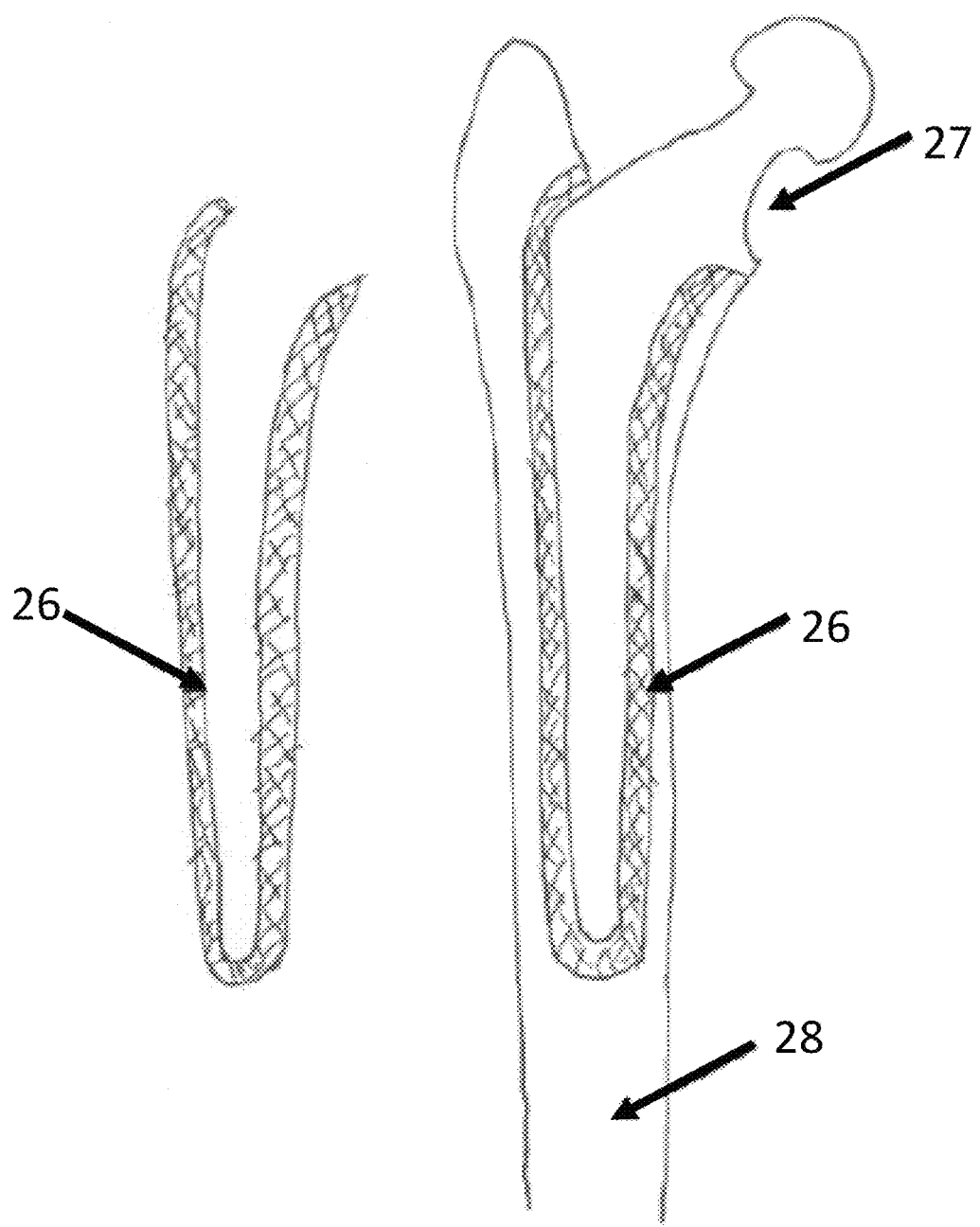
FIG. 12 shows a DBF implant 26 formed in a shape that surrounds the hip stem and forms an interface between the hip stem 27 and surrounding bone 28, according to some embodiments of the present invention.
Figure 24:
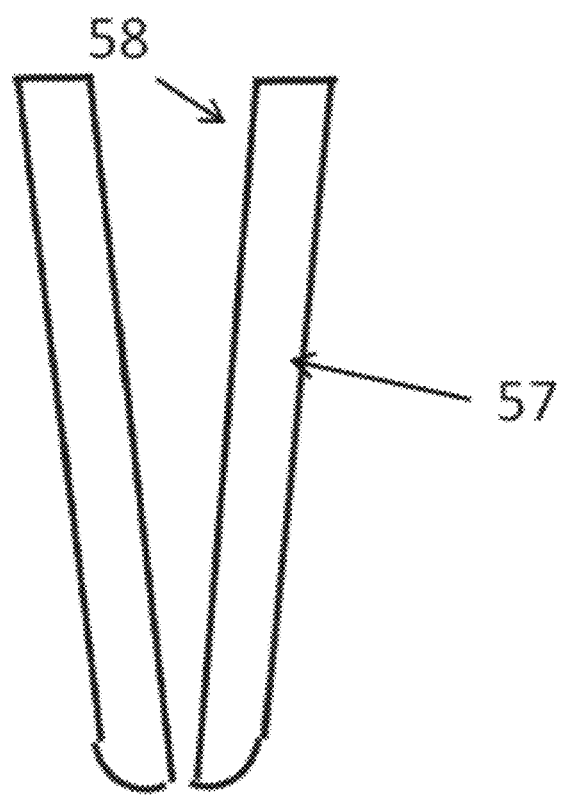
FIG. 24 shows the cross section of an implant of this invention for use in acl augmentation. The implant is a truncated cone 57 wherein the distal end is narrower than the proximal end. The central cannulated region 58 is flared so that the opening at the proximal end is greater than at the distal end.
Figure 29:
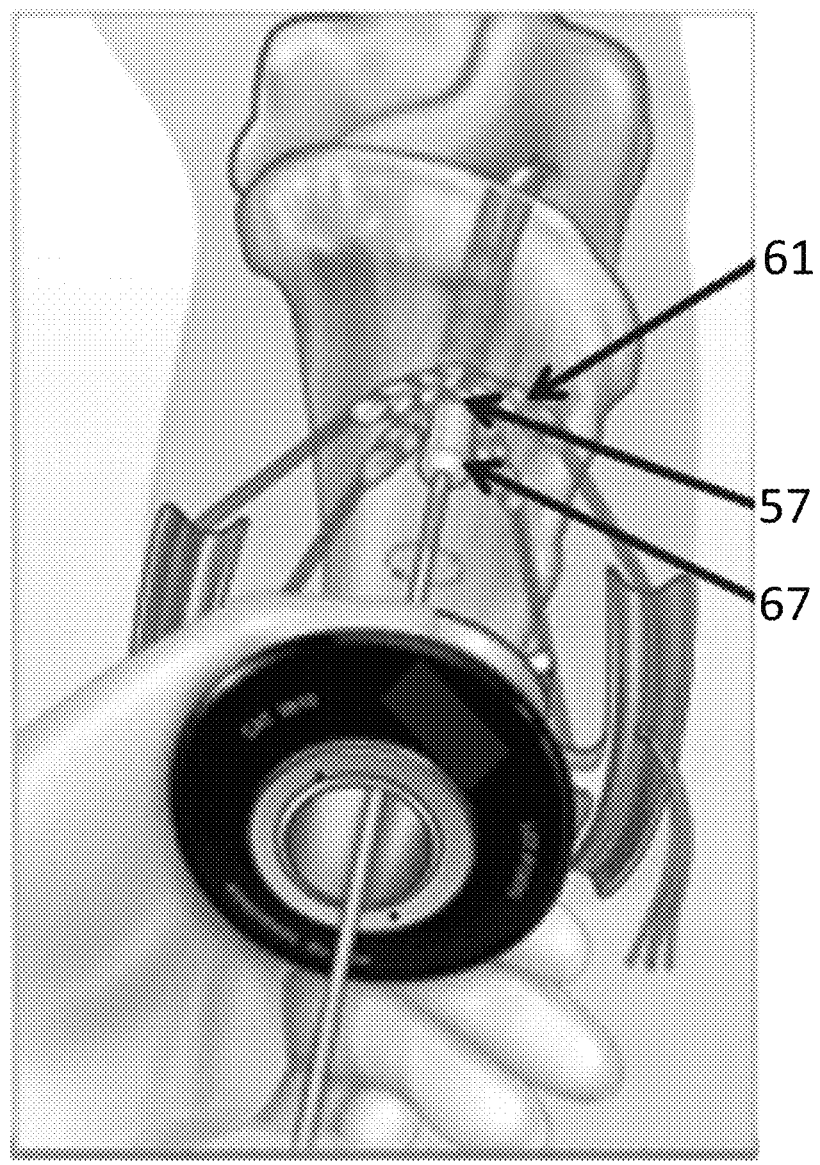
FIG. 29 shows the surgical use of the device of FIG. 24. The device 57 is placed within the four strands 61 of a tendon graft before being pulled into the tibial tunnel. An interference screw 67 is then inserted within the device.

As an alternative method of augmentation that is particularly suited to the tibial tunnel a cone shaped implant 57 such as is shown in FIG. 24 may be placed within the four strands of the graft, as is shown in FIG. 29. The interference screw is then inserted inside the implant and screwed into place to affect fixation of the tendon Augmentation of other tendon and bone interfaces may also be effected by use of sheets of DBF. FIG. 1I is a diagram showing a rotator cuff repair wherein the DBF sheet 22 is placed onto the bone bed between the bone 24 and the tendon to be reattached 23. The nature of the DBF sheet is such that conventional suture anchor fixation techniques do not need to be modified. In FIG. 11 the repair may be seen to be affixed using the sutures 25a together with the suture anchors 25b.

Rotator cuff repair is generally done as an arthroscopic procedure and so the joint is inflated with saline to aid visualization. There are a number of patch products used for reinforcement of the tendon, and while this is not the intended application for the DBF sheet in the aforementioned example, our sheet will be subject to similar difficulties in use that all patch products have, namely that their buoyancy leads to them tending to float around in the joint. Manipulation of these sheets arthroscopically is extremely difficult adding time and complexity to the surgery. This can exclude some surgeons from being able to use the products due to the degree of difficulty. In some instances, sophisticated, (i.e. complex and expensive), ancillary instruments are developed in an attempt to make the use of sheet products easier.

Aspects of the inventive subject matter include an augmented implant wherein an implant (e.g., a sheet implant) is modified to have a stabilizing portion. The stabilizing portion may increase the effectiveness of sutures used to place the implant for the needed surgical repair. Furthermore, the stabilizing portion may increase the stability of the implant while the implant is being surgically placed and/or tethered into place. For example, the stabilizing portion may be a peg portion. The peg portion may be solid or tubular (e.g., hollow) with an open and closed end.

Accordingly, the inventors of the presently disclosed subject matter have discovered an advantageous implant that is at once capable of: 1) serving as a patch for the bone site to be repaired. 2) augmenting the effectiveness of the suture anchor, and 3) self-stabilizing during surgery unlike other implants. Accordingly, aspects of embodiments of the present invention are directed to a means of improving the fixation of implants and tissue to bone through the use of an implant, which may, for example, be composed of fibers of demineralized bone and formed into an appropriate shape. In particular, the implant made of a plurality of fibers has peg portion and sheet portion.

Figure 30A:
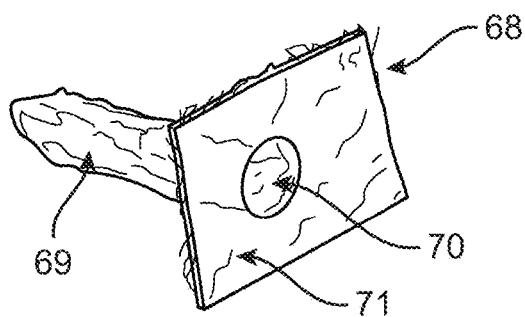
FIGS. 30a-30d show a device to augment reattachment of tendon to bone. The device 68 that is fabricated from demineralized bone fibers is shown in FIG. 30a. The device has a "peg" 69 that is intended to be placed in a hole in bone, a cavity 70 within that peg that is designed to receive a suture anchor, and a sheet region 71 that is intended to sit between tendon and bone.
Figure 30B:
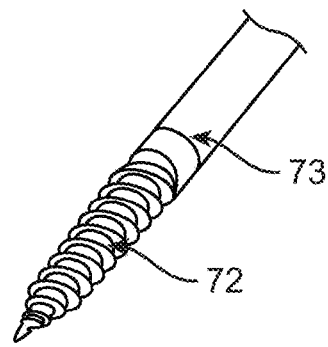
Figure 30C:
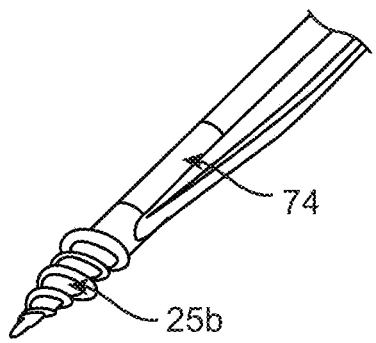

The implant device 68 shown in FIG. 30a overcomes the problems associated with the manipulation of sheet-like devices in the joint. The sheet portion 71 of the device has a "peg" 69 that is formed onto it. The peg has a cavity 70 that receives a suture anchor 25b. The surgical technique by which these implants are used is that a dilator 72 or other instrument is used to form a cavity. A mark 73 on the dilator serves to allow the surgeon to get the desired depth of cavity. Suture anchors 25b for use in arthroscopic surgery are generally supplied pre-loaded with suture and attached to an insertion driver 74. The peg 69 on the device is sized to match the dimensions of the cavity formed using the dilator and the cavity 70 in the device is sized to receive the suture anchor 25b. The suture anchor is inserted into the cavity 70 and turned slightly to engage the threads of the anchor into the device. This served to lock the device onto the suture anchor. The suture anchor driver can then be used to manipulate the peg part of the device into the cavity in the bone.

The sheet or top portion of the device is sized so that when multiple suture anchors are used that the multiple devices that are used form a contiguous sheet at the tendon bone interface. Thus, if for example the surgeon desired a 10 mm spacing between suture anchors then the device selected would be 10 mm wide or would be trimmed to 10 mm wide so that adjacent device/suture anchor combinations would form a contiguous sheet. Similarly, if a double row fixation technique were to be employed where there were two rows of suture anchors then the dimension of the sheet portion of the device would be sized appropriately such that a non-overlapped contiguous sheet were formed.

Figure 31A:
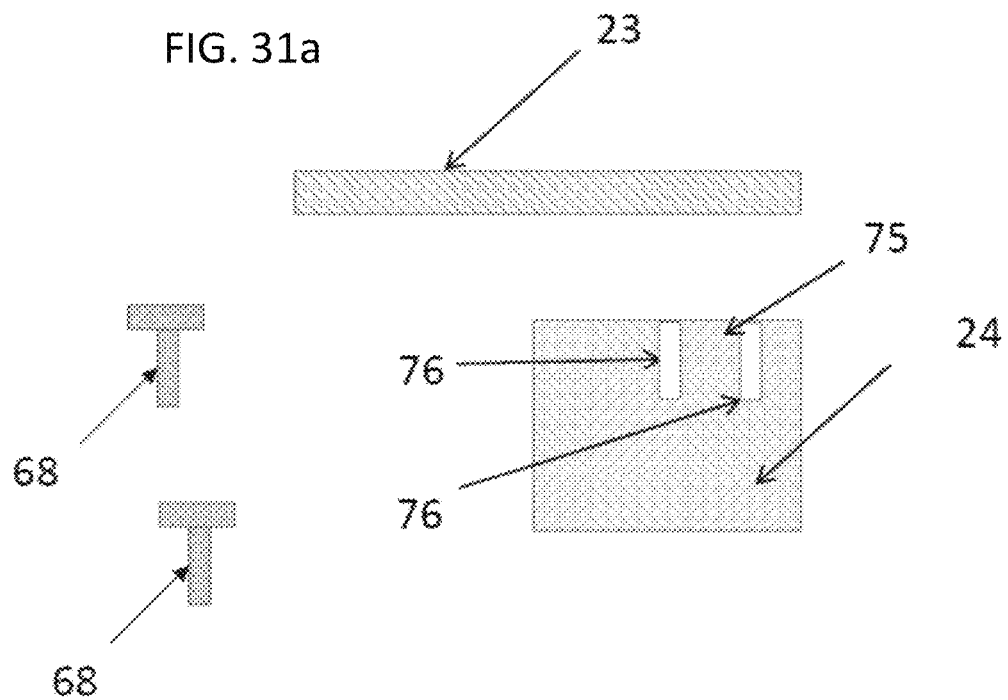
In FIG. 31a the bone 24 has been prepared to receive two devices 68. Two holes 75 have been made in the bone.
Figure 31B:
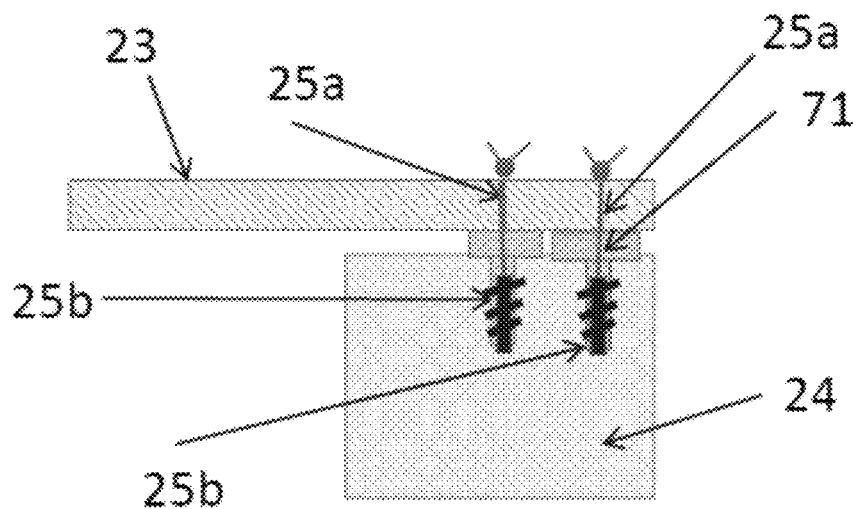
In FIG. 31b the suture anchors 25b have been used to introduce the devices 68 into the bone and the suture 25a has been used to re-attach the tendon 23 to the bone. The sheet region 71 of the device is sited between the tendon 23 and bone 24.

FIG. 31b shows the first steps in the surgical technique. The surface of the bone where the tendon is to be re-attached 75 is treated with a burr or similar to form a bleeding bone bed to maximize healing potential, as is normal practice. A dilator, or similar (not shown) is used to produce cavities 76 to receive the device 68 and suture anchor. As described above the suture anchor is inserted into the device 68 and rotated to engage the anchor threads into the device and lock the two together. The device is inserted into the cavity 76 and pushed down to fully seat it. The suture anchor is then screwed in. The anchor driver is removed leaving the sutures ready to be used. Additional anchors and devices are inserted, as required by the size of the tear being repaired. The device is held in place by the suture anchor and the completion of the surgery requires no additional manipulation of the device. To complete the repair, the current procedure of passing the sutures through the tendon and using them to reapproximate the tissue before knot tying is done. The device is sandwiched between the tendon at the bone where it can have the desired effect of stimulating an improved enthesis regeneration.

The preferred embodiment of this device is dried or lyophilized. In this form the device is stiff and insertion into the cavity is easiest.

An additional benefit of the device 68 is that the peg portion of the device serves to augment the fixation strength of the suture anchor. This is especially important when the patient's bone quality is poor. It may also allow the surgeon to use a smaller diameter suture anchor.

The peg portion of the device 68 is designed to be compatible with the suture anchor it is to be used with. As such the length of the peg corresponds to the depth of the cavity required for the suture anchor and may vary from 10 to 50 mm. Similarly, the diameter of the peg corresponds to the diameter of cavity required for the suture anchor and may vary from 3 to 10 mm.

The sheet portion 71 of the device is sized such that when a multitude of suture anchors are used that the bone bed 76 is fully covered. This may be achieved by the surgeon trimming devices to the required size prior to use, or by selection of the appropriate size from an available range of product sizes. The sheet portion may be rectangular, square or round. For square and rectangular devices the side dimensions will vary from 5 to 20 mm. For round devices the sheet portion will be 5 to 20 mm in diameter. The thickness of the sheet portion of the device will vary from 0.5 mm to 5 mm.

By using the suture anchor as the delivery device for the implant the need for additional instruments is avoided. The design, by using the anchor hole to provide initial fixation of the device, provides a very simple means of introduction of a sheet device, and of holding it in the desired place without the need for any additional instruments, or additional portals into the joint.

By sizing the top portion, or sheet, of the device to be compatible with the spacing used between suture anchors the need for multiple sizes of device is avoided. This additionally means that the waste associated with cutting larger sheet implants to the desired size is avoided.

While this modular approach to covering the enthesis is preferred, if desired a larger sheet implant could be provided that had one or two pegs.

While the examples given for use of this design were for rotator cuff repair it will be understood by one skilled in the art that the applicability is more general than this and is applicable to any instance of tendon to bone reattachment or repair, or any instance where a sheet implant needs to be held in place during surgery. Accordingly, the inventors further contemplate augmenting any sheet implant with a peg portion to thereby facilitate the surgical placement of the implant. It is contemplated that any existing sheet implant may be improved by modifying an already manufactured sheet implant or by modifying the manufacturing protocols of the existing sheet implant to incorporate a peg portion to produce an implant having improved stability during surgical placement.

In some embodiments of the present invention, a DBF sheet may be used for augmentation of bone-to-bone repair either in a primary fracture repair or in a procedure to remedy a non-union. In these instances, the DBF sheet will form a malleable interface between the two (or more) bone fragments.

A DBF sheet may also be wrapped around the periosteum to hold bone fragments or graft in place in traumatic fractures and may act as a periosteum substitute. The osteoinductive and osteoconductive nature of the DBF sheet will facilitate healing.

In many joint replacements a stem is placed into a cavity created in the intramedullary canal. It is often desired to enhance the integration of implants such as total hip or shoulder replacements to the surrounding bone. DBF may be formed into a sheath 26 that conforms to the shape of the implant stem 27. The DBF may then provide for augmentation, or stimulation of fixation, of the stem to the surrounding bone.

A further issue that may occur is that, particularly in the case of revision surgery, there is insufficient bone and the surgeon may require the use of bone graft. In these instances, the DBF sheath may be provided in a range of thicknesses up to several mm in thickness to provide for use as a bone graft substitute.

In some embodiments of the present invention, the sheet form of DBF may be used to augment the fixation of tibial tray and acetabular cup components of joint replacements. In this latter instance the sheet may be molded into a cup shape.

In some embodiments of the present invention, the DBF used in an implant uses bone that has had the mineral component removed by a demineralization process that renders the graft malleable and not hard. The bone is then further formed into fibers by cutting along the long axis such that the collagen fibers within it are maintained in their natural fibrous form, as disclosed in U.S. Pat. Nos. 9,486,557 and 9,572,912, supra. This material may then be placed into tubes to form the implant device and to facilitate delivery into the screw hole.

A number of methods of forming cylindrical implants from DBF are also disclosed in WO 2016/123583, the entire content of which is herein incorporated by reference.

In some embodiments, the methods for making the bone fibers include demineralizing whole bone and subsequently cutting the demineralized bone in a direction parallel to the orientation of collagen fibers within the demineralized bone to form elongated bone fibers. The bone material of the present invention is derived from human (allograft) or animal (xenograft) cortical bone and is processed in such a manner to provide grafts of high utility based on the controlled geometry of the bone fibers. For veterinary applications bone from the same species. e.g., canine for canine patients (allograft) may be used as well as bone from other species (xenograft). It will be obvious to one skilled in the art that fibers other than demineralized bone fibers may be utilized to make a bone graft of this invention. Such fibers may be made from resorbable polymers or bioactive glasses or mixtures thereof, and may be used in place of or as an additive to the demineralized bone fibers (DBF). The methods of preparation of the graft provide improved efficiency and uniformity with reproducible results and decreased requirements for equipment and resulting costs. The implant device forms according to some embodiments of the present invention do not require the addition of exogenous materials to maintain the form of the graft. These improved characteristics will be apparent to one skilled in the art based upon the present disclosure.

The fibers need to have greater than a minimum length to be able to function effectively. If they are too short, they will not entangle to form a cohesive dry implant. Also to prevent movement in the cavity post implantation, and after screw placement, they need to be longer than the pitch of the screw thread so that the screw holds them in place. The minimum length cannot be precisely defined but is approximately 15 mm (e.g., between 10 and 20 mm). Fibers up to 4 cm in length have sufficient length to provide entanglement and are preferably 500 to 1500 microns in width and 50 to 300 microns thick.

It is also important to a number of the applications that the DBF can be dried to render a stiffer implant at the time of implantation.

A further benefit of the DBF fibers is their ability to be processed to form an implant that retains its integrity when wet.

Processing of Fibers

Processing of the demineralized bone fibers, synthetic polymer fibers, collagen fibers, or resorbable polymer fibers to produce a desired shape or form of the fibers may be performed using any suitable method. Processing of specifically demineralized bone fibers may be performed using any suitable method as disclosed herein. To make some of these forms, the bone fibers may be collected, ideally in their hydrated state, and compressed using pressure molds, the pressure being sufficient to form the required shape but not so high as to lose the porosity of the fibrous structure. In some embodiments, the bone fibers are formed using a wet lay technique as is well understood by those skilled in the art of nonwoven or paper manufacture. Using a wet lay technique, the cut bone fibers are suspended in an aqueous solution to form a bone fiber slurry. Any suitable biocompatible aqueous solution may be used. Non-limiting examples of biocompatible aqueous solutions include: water, saline, and/or solutions including salts such as phosphate buffered saline (PBS). Ringer's solution, Lactated Ringer's solution, and saline with 5% dextrose. In some embodiments of the present invention, cut fibers are placed into saline to create a slurry of entangled bone fibers. The bone fiber slurry is suspended over a mesh screen (having holes) and the saline is drained resulting in a wet lay process, such that a sheet of demineralized bone fibers is formed on the mesh screen. The screen is contoured to provide a three-dimensional shape to the screen such that cylindrical pellets may be directly produced, or is flat so that a sheet is produced. The resulting devices may be then dried using heat and/or vacuum or other means such as lyophilization (freeze-drying). In some embodiments, prior to drying, the sheet is placed in a mold and compressed to a defined thickness and shape, followed by drying. As discussed herein, density, porosity and overall dimensions of the resulting product may be controlled using various molds and techniques.

Figure 4:
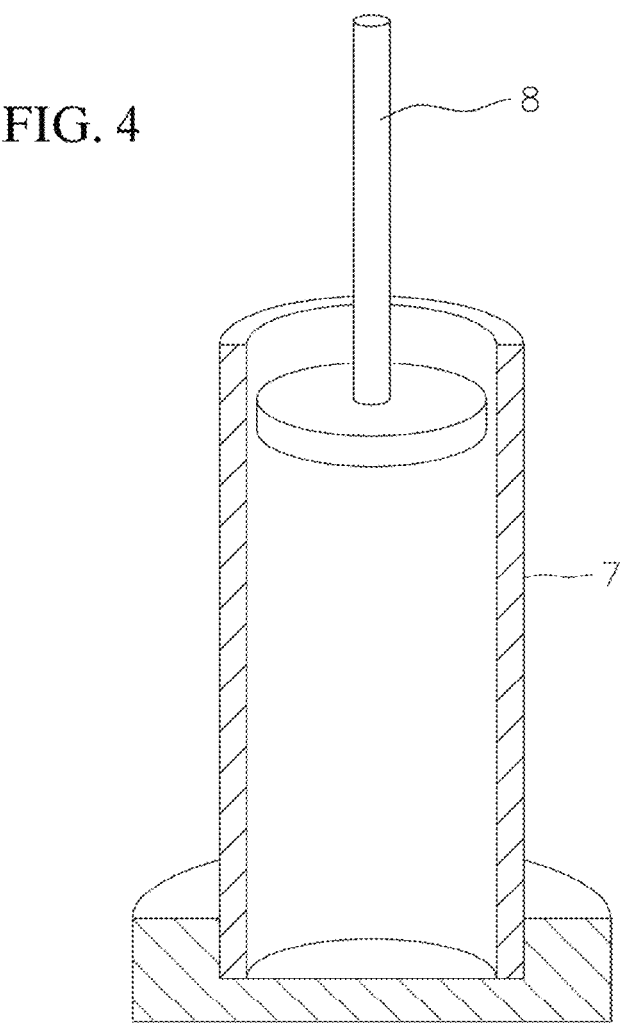
FIG. 4 shows a cylindrical mold 7 and plunger 8 designed to produce cylindrical implants, according to some embodiments of the present invention.
Figure 5:
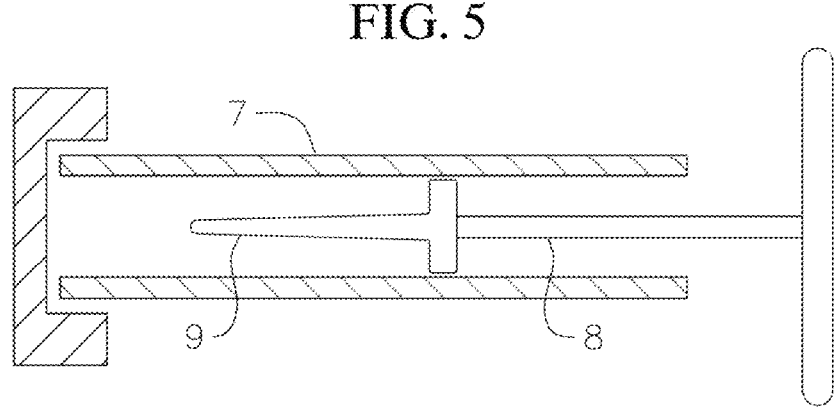
FIG. 5 shows a variant of the mold 7 of FIG. 4 wherein the plunger 8 has a spike 9 that produces a central depression in the implant to facilitate central screw insertion, according to some embodiments of the present invention.
Figure 6:
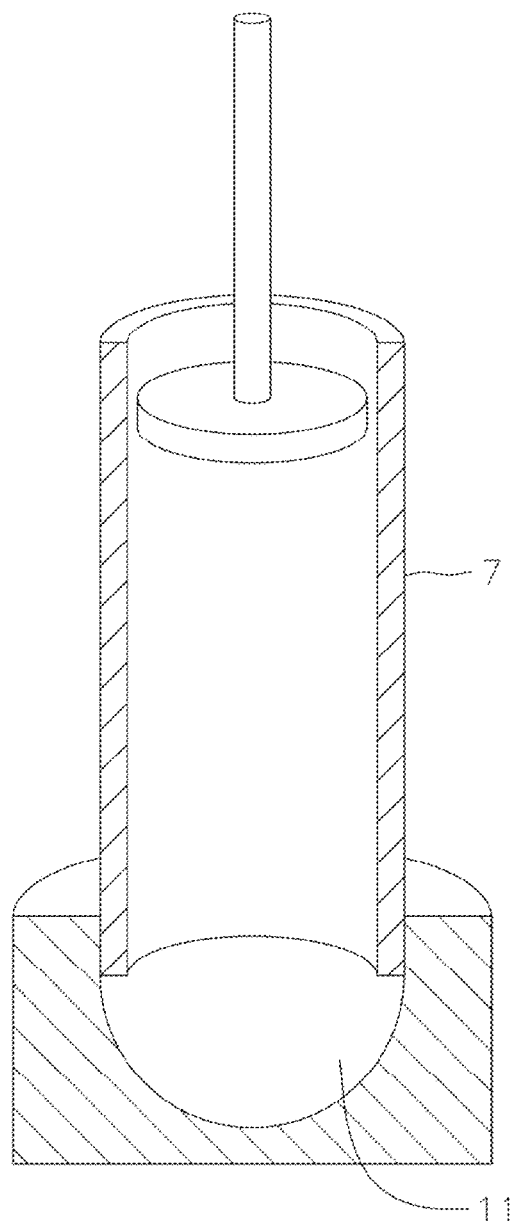
FIG. 6 shows a further variant of the mold 7 of FIG. 4 wherein the distal end of the cylindrical mold 7 has a domed depression 11 to provide a domed implant, according to some embodiments of the present invention.
Figure 9:
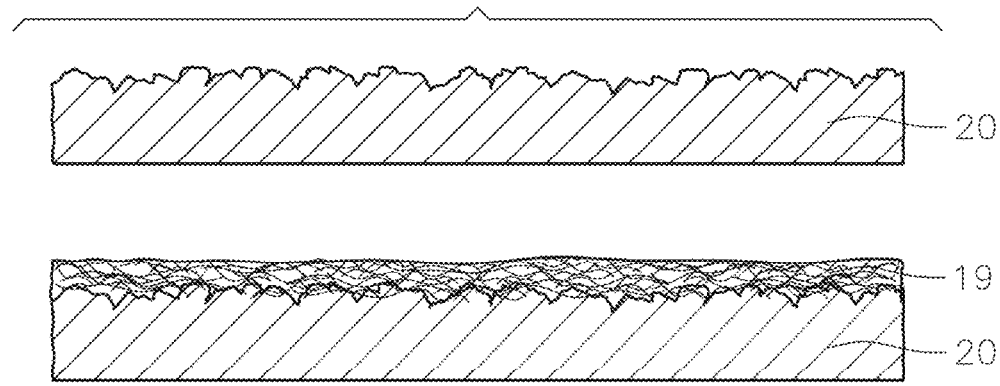
FIG. 9 shows a sheet of DBF 19 formed onto the porous surface of an implant 20, according to some embodiments of the present invention.

Hydrated fibers may also be simply placed into a cylindrical mold cavity and lightly compressed using a plunger or push rod such as is shown in FIGS. 4, 5 and 6. In these variants features are provided to modify the profile of the two ends of the cylindrical mold. A set amount of fiber is introduced into a cylindrical mold and the plunger used to compress the fibers to the required density through control of the depth that the plunger is pushed. Where a plunger has a spike on it, such as is shown in 6 of FIG. 9 the spike may be designed to form a depression, a partial hole, or a hole through the length of the implant. In this latter instance the implant will be in the form of a tube.

In some embodiments a vacuum oven is used, whereby the application of vacuum removes moisture and dries the implant.

In some embodiments the heating step is undertaken by placing the implant in contact with a metal or other high heat-conductivity surface such that the degree of annealing/crosslinking is enhanced at that surface.

In other embodiments, the bone fibers are further processed in a second drying step that may include vacuum drying and/or lyophilization.

In some embodiments the amount of compression, heating, and drying can be tailored to modify the rehydration and re-expansion rates. For example, with no heating the rehydration is very fast whereas heating at or between 35° to 55° or 45° to 55° C. for approximately one hour causes very slow re-hydration and re-expansion. In other aspects, the heating may occur at any of 35°, 36°, 37°, 38°, 39°, 40°,41°, 42°, 43°, 44°, 45°, 46°,47°, 48°, 49°, 50°, 51°, 52°, 53° 54°, or 55° C. By altering these processes, bone fiber compositions as disclosed herein may retain their manufactured shape during packaging, shipment, unpacking and placement into the graft site, but after placement into the graft site the DBF will begin to absorb moisture rapidly (within 30 seconds or less) and may be completely re-hydrated/re-expanded within approximately 2 minutes, preferably being completely re-hydrated/re-expanded within 30 seconds.

In other embodiments the bone fibers may retain some moisture and will be placed in moisture impervious packaging. Furthermore, the dried and molded bone fiber implant may be sterilized after packaging. Sterilization of the implant may be carried out using any suitable method. For example, sterilization may be carried out by electron beam or gamma beam. Alternatively, aseptic manufacture may be used to avoid the need for terminal sterilization.

In other embodiments, the inventive subject matter also includes a simple mold of the sort shown in FIG. 8 may be used to make DBF sheets of 0.5 mm to 5 mm thick, where the mold lid may be placed on the mold 17 (the mold having holes for drainage of the liquid in the DBF slurry) where the lid is in contact with the DBF after the DBF has been wet laid and may define the degree of compression of the DBF and hence the density of the sheet.

A DBF sheet that is dried will have a low wet strength when rehydrated and improvement to the DBF sheet wet strength may be affected by placing the mold in an oven at 45-55° C. and heat treating the sheet for up to 2 hours.

In some embodiments, bone fiber pellets are formed by adding wet fibers directly into a cylindrical mold. An example of a cylindrical mold is a metal tube as is shown in FIG. 4. A bone fiber pellet shape is useful as it may be delivered to a graft site using a cannula as commonly used for minimally invasive surgery. The bone fiber pellets are capable of passing through a tube. A cylindrical mold is loaded with the fiber. A tamp is used to apply some compression to the fibers. In some embodiments, a fiber loaded cylindrical mold is dried by heat, vacuum, and/or lyophilization. After drying, the bone fiber implant becomes more cohesive and shrinks to a reduced volume. After drying, the bone fiber pellets may be easily expelled out of the mold due to the shrinkage that occurs upon drying.

While wet lay techniques may be used for the manufacture of different shapes from the bone fibers, it will be recognized that any other molding or forming technique used with textile fibers could be used. Fibers with and without excipients may be directly molded using compression into any shape. In some embodiments, excipients may be selected that enhance the lubricity of the implant facilitating delivery and further reducing and friction or binding during this procedure.

Figure 7:
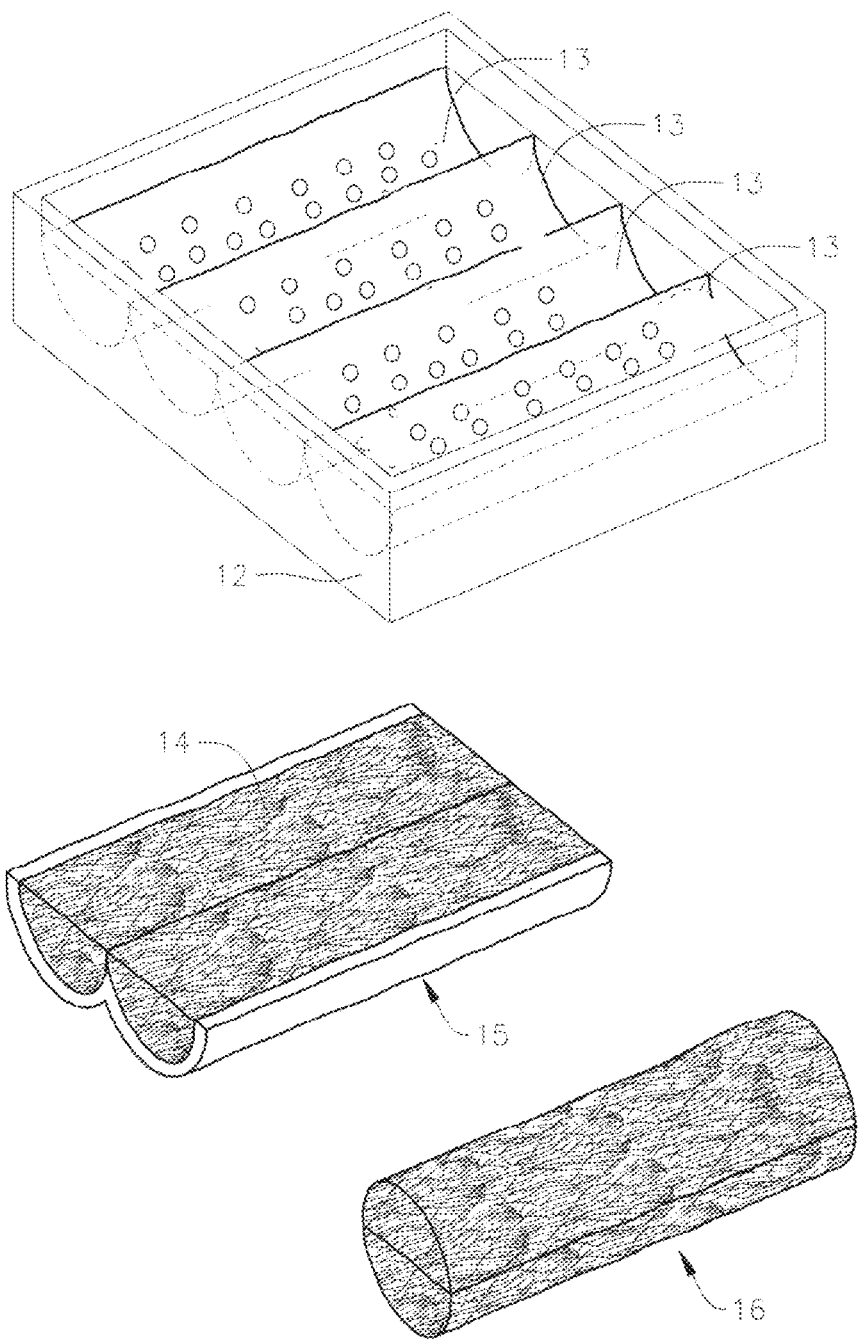
FIG. 7 shows a mold 12 with semi cylindrical depressions 13. DBF is wet laid into a mold and the implant is formed from two conjoined semi cylindrical depressions. The implants 14 may be stored in this manner in a flexible storage tray 15 and at the time of surgery may be folded together to produce a cylindrical implant 16, according to some embodiments of the present invention.

Long cylindrical implants may not be easily produced using a conventional wet lay process. As an alternative method, implants may be wet laid into a mold 12 with two conjoined semi cylindrical depressions having drainage holes throughout as shown in FIG. 7. The implants 14 may be stored in this manner in a flexible storage tray 15 and at the time of surgery may be folded together to produce a cylindrical implant 16.

Alternatively, semi cylinder implants produced in a mold such as shown in FIG. 7 may be folded together post wet lay and prior to the heat treatment step. At this time the two halves of the cylinder will become entangled and bonded to each other.

Alternatively implants for augmentation of screw fixation may be formed in two halves, such that the implant is folded about the part that becomes the implant's distal end. A selection of such designs are shown in FIGS. 15a-15i. The simplest format is a rectangular prism 31. Variants are shown as follows: in FIG. 15b where a central portion 32 is densified to provide it with increased strength; in FIG. 15c where the cross-section 33 is semi-circular; in FIG. 15d where the rectangular prism is narrower at the center 34; and FIG. 15e where the rectangular prism is both narrower at the center 34 and possesses a semi-circular cross-section 33. FIG. 1f shows a side view cross-section of a drill hole 35 with an implant 31 inserted, the insertion being effected by use of a pusher 36. The implant is longer than is required to fit the hole. FIG. 15g shows a side view cross-section of a drill hole 35 with an implant 31 inserted, the insertion being effected by use of a pusher 36 in which the implant 31 is the exact length or about the length necessary to fit in the hole without protruding out of the hole. Additionally, FIG. 15h is an end view looking down the hole to show that the implant shown in FIG. 15c forms a space-filling implant when inserted into the hole. And FIG. 15i is a cross-sectional view of the implant of FIG. 15e inserted into a tapered hole where the shape of the implant is designed to be space-filling in a tapered hole.

With continued reference to FIGS. 15a-15i, implants of these designs may be fabricated using a wet lay method with a mold that has depressions that define the required implant dimensions. The DBF may be heated to a temperature of between 40° and 53° C. for 30 to 150 minutes to dry the implant and to improve the cohesion of the fibers. After drying the individual implants are cut out of the wet lay mold.

Figure 15B:
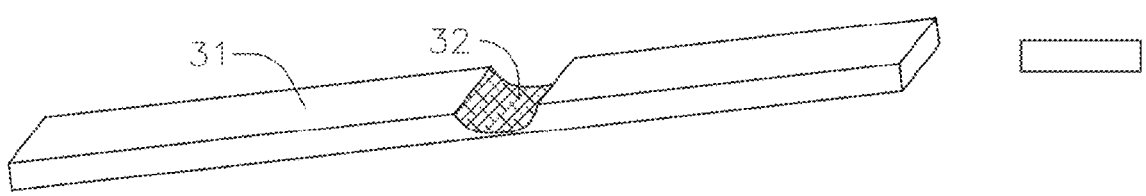
FIG. 15b shows a variant of the implant of the present disclosure, where a central portion 32 is densified to provide it with increased strength, according to some embodiments of the present invention.
Figure 15C:
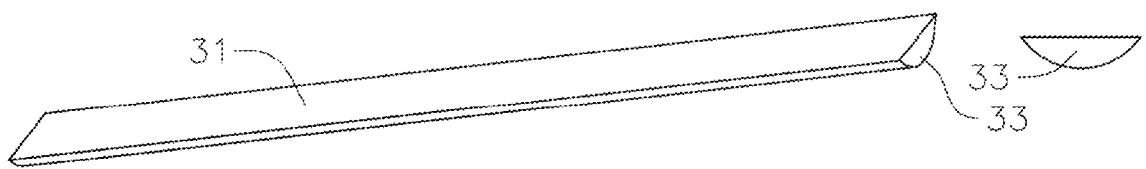
FIG. 15c shows a variant of the implant of the present disclosure where the cross-section 33 is semi-circular, according to some embodiments of the present invention.
Figure 15D:
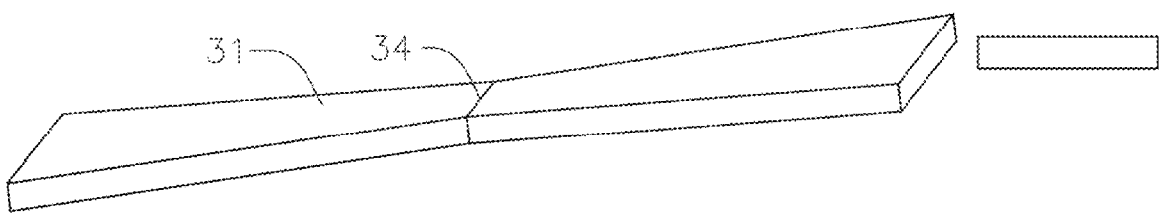
FIG. 15d shows a variant of the implant of the present disclosure where the rectangular prism is narrower at the center 34, according to some embodiments of the present invention.
Figure 15E:
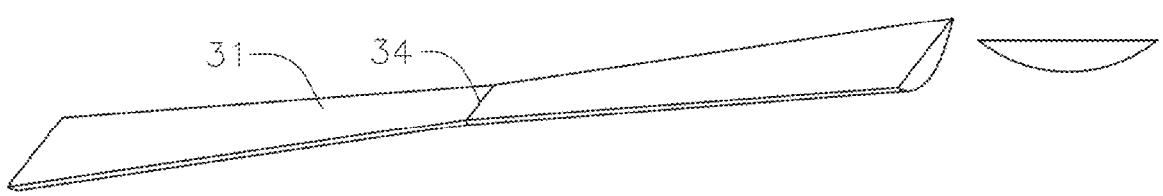
FIG. 15e shows a variant of the implant of the present disclosure where; the rectangular prism is both narrower at the center 34 and possesses a semi-circular cross-section 33, according to some embodiments of the present invention.
Figure 15F:
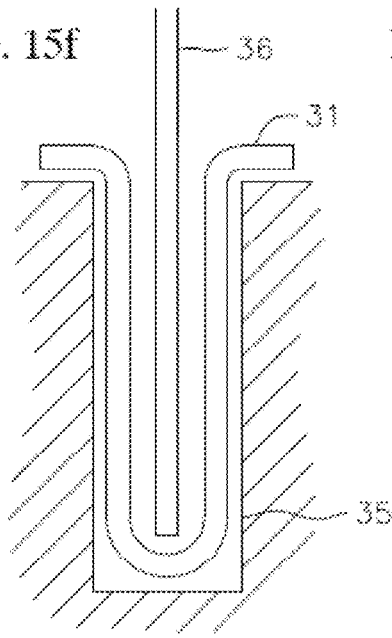
FIG. 15f shows a variant of the implant of the present disclosure where a side view cross-section of a drill hole 35 with an implant 31 inserted, the insertion being effected by use of a pusher 36, where the implant is longer than is required to fit the hole, according to some embodiments of the present invention.
Figure 15G:
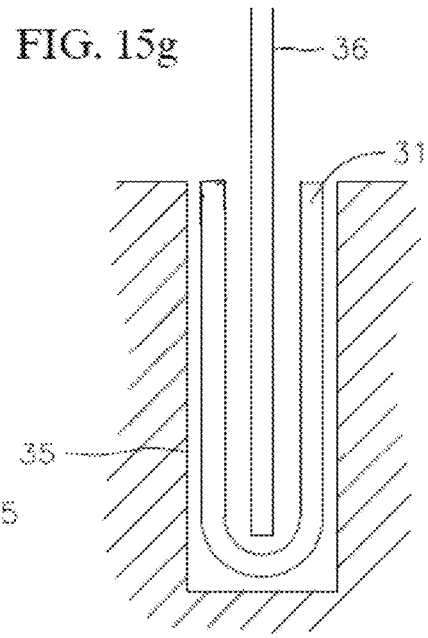
FIG. 15g shows a side view cross-section of a drill hole 35 with an implant 31 of the present disclosure inserted, the insertion being effected by use of a pusher 36, Where the implant is the exact length that is required to fit the hole, according to some embodiments of the present invention.
Figure 15H:
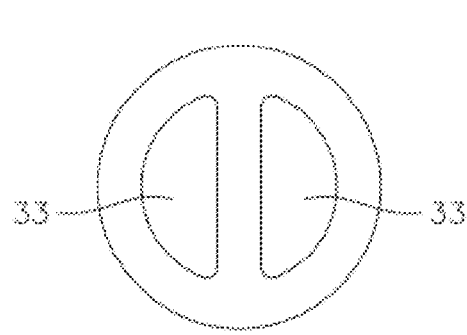
FIG. 15h is an end view of the implant of FIG. 15c looking down the hole to show the implant forms a space-filling implant when inserted, according to some embodiments of the present invention.
Figure 15I:
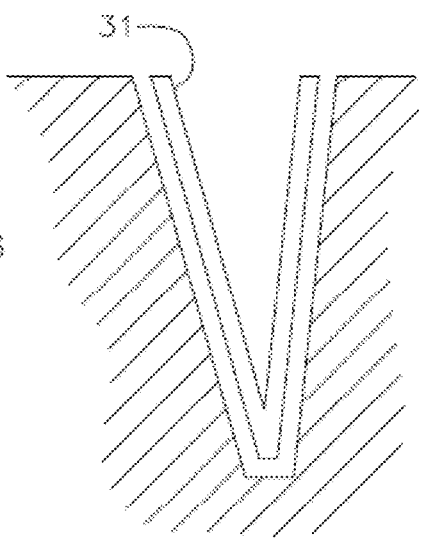
FIG. 15i is a cross-sectional view of the implant of FIG. 15e in a tapered hole where the shape of the implant forms a space-filling implant in the tapered hole, according to embodiments of the present invention.

Using the implant designs according to embodiments of the present invention allows for facilitated insertion of the implant into holes by use of a pusher that acts upon the fold of the implant, as shown, for example in FIG. 15b, 32.

There are particular difficulties that are encountered when trying to make implants of the size and shape required to be used in augmentation of screw fixation in orthopaedic and spine surgery. The desired or required implant dimensions are approximately 2 to 7 mm diameter and 1 to 7 cm long. To enable the implant to have sufficient mechanical integrity and for the implant to be implantable, the DBF fibers must be of a sufficient size to provide a cohesive implant. The currently available DBF are approximately 4 cm long and 500 to 1000 microns wide are able to provide the mechanical integrity, however the fiber size provides a difficulty in processing the DBF into the required sizes using the heretofore-identified manufacturing methods. This problem is exacerbated when the implant is less than approximately 5 mm in diameter and is required to be longer than 1.5 cm. The fabrication of the implant of Example 1 below, while possible, was an extremely time consuming and difficult process, and is not conducive to an efficient manufacturing process. Furthermore, molding parts of the designs shown in FIGS. 15a-15i require that the wet laid DBF is wet laid into the grooves of the mold rather than across them. If the fibers cross from one implant cavity to another then the fiber will be cut when the part is removed from the mold. If this occurs for too many fibers, then the cohesive strength of the part will be lost. For these reasons, there is a size of approximately 5 mm width, below which implants cannot be produced using this methodology.

The wet lay process was originally developed for use in paper making and textiles where the fibers are processed to make a two-dimensional sheet like product. As the fluid drains the fibers are laid onto the surface of the mold and as such are in a plane that is generally parallel to the plane of the sheet being produced. While this process can accommodate some undulations and be used to make shapes like egg cartons it is wholly unsuitable for the fabrication of cylindrical shapes.

According to embodiments of the present invention, by dispersing fibers in an excess of fluid, the fluid and fibers may be directed into molds of small diameter and long length. Implants that are about 2 to about 5 mm in diameter and about 4 to 5 cm in length have a volume of 0.15 cm$^3$ up to 10.0 cm$^3$. Typically, the volume of the implant is about 0.15 cm$^3$ up to 2.0 cm$^3$. Additionally, the length of the implant may be of between 2 cm in length up to 10 cm in length depending on the need of the bone repair site. The length of the implant may be of between 3 cm and 10 cm in length, 4 cm and 10 cm in length, 4 cm and 9 cm in length, 4 cm and 8 cm in length, 4 cm and 7 cm in length, 4 cm and 6 cm in length, or 4 cm and 5 cm in length. For receiving and fixing a bone screw, the implant (e.g., 31 of FIG. 15*i*, or 68 of FIGS. 30*a* and 30*d*), may have a length corresponding to the length of the bone screw. Accordingly, the length of the implant having a cone, tubular, or cannulated shape may have a length suitable for receiving a bone screw or any bone repair material including additional demineralized bone fibers (DBF).

The required mass of DBF to fill those molds is approximately 0.15 gram to 1 gram and may be dispersed in about 20 mls of fluid in a syringe, in a ratio of fibers to fluid as disclosed herein. Dispersion of the fibers in fluid into the molds may be by injection pressure or by vacuum as well as gravity as needed. Any suitable fluid buffer may be used. For example, phosphate buffered saline (PBS) may be used for dispersion of the fibers as well as water or any biocompatible buffer or liquid.

In contrast to conventional methods of fabrication, rather than rely on gravitational flow, an elevated pressure is applied to the dilute fiber and fluid dispersion. This forces the fibers to flow down narrow diameter structures rather than form an entangled clump at the entrance to the mold cavity. Because the fibers are dispersed, they do not compact when introduced into the mold. Accordingly, the slurry suspension of fibers is advantageously introduced and place in the mold because the fiber suspension is injected or pushed into the mold at a rate greater than a gravitational flow, but not so much pressure/force that the fibers clump or compact. For example, a 15 ml slurry of a fiber suspension having a ratio as disclosed herein is introduced into a mold in about 1 to 5 seconds. As such, the slurry of fibers are placed or provided into the mold at a rate from about 3 mls/second up to 15 mls/second.

Figure 16:
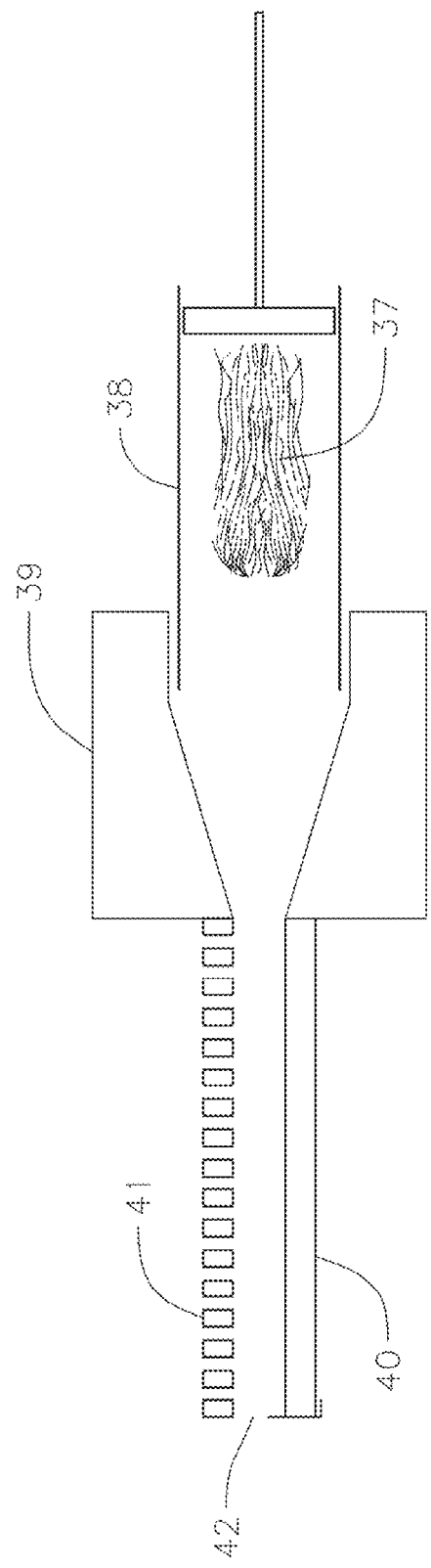
FIG. 16 shows a cross-section view of an apparatus for water assisted injection molding of DBF fibers, where the DBF fibers 37 are loaded into a syringe 38, the distal end of the syringe is fitted into an adapter 39, attached to which is a detachable mold 40, where the mold is tapered towards its distal end and has vents 41 along its length, and a removable vented end cap 42, and the detachable mold is removed after DBF injection and placed into an oven or lyophilizer for drying, according to some embodiments of the present invention.

FIG. 16 depicts an apparatus for water- or fluid-assisted injection molding of DBF fibers. The required mass of DBF fibers 37 are loaded into a syringe 38. A suitable fluid (e.g., water, saline, or a buffered saline including phosphate buffered saline (PBS) is then added to the syringe. The distal end of the syringe is then fitted into an adapter 39 to which a detachable mold 40 is attached. The mold renders the required dimensions of the implant to be made, and the mold may be cylindrical, ribbed, and/or tapered. As with conventional injection molding, the cylinder will have a small taper or draft to allow removal of the molded part. The mold is tapered towards its distal end and has vents 41 along its length, and a removable vented end cap 42 to allow for the fluid to egress out of the DBF mixture. The detachable mold is removed after DBF injection and placed into an oven or lyophilizer for drying. Multiple molds may be used with one adapter and syringe to allow multiple parts to be fabricated.

In some embodiments of the present invention, the ratio of fluid (e.g., saline) to DBF may be about 3 mls fluid to 1 gram DBF. In other embodiments, the ratio of fluid to DBF is about 3, 4, 5, 6, 7, 8, 9, 10, 11, 12, 13, 14, 15, 16, 17, 18, 19, 20, 21, 22, 23, 24, 25, 26, 27, 28, 29, 30, 40, 41, 42, 43, 44, 45, 46, 47, 48, 49, or 50 mls fluid to 1 gram of DBF. In still other embodiments, the ratio of fluid to DBF is less than about 200 mls fluid to 1 gram DBF. Advantageously, a ratio of fluid to DBF being in the range of between about 3 to 200 mls fluid to 1 gram DBF, 3 to 150 mls, 3 to 100 mls, 3 to 50 mls, 3 to 20 mls, or 3 to 10 mls all provide enough fluid to hydrate the DBF to facilitate shaping and forming of the DBF implant into the desired shape while also allowing for complete removal of the fluid to produce a dry DBF implant.

Figure 17:
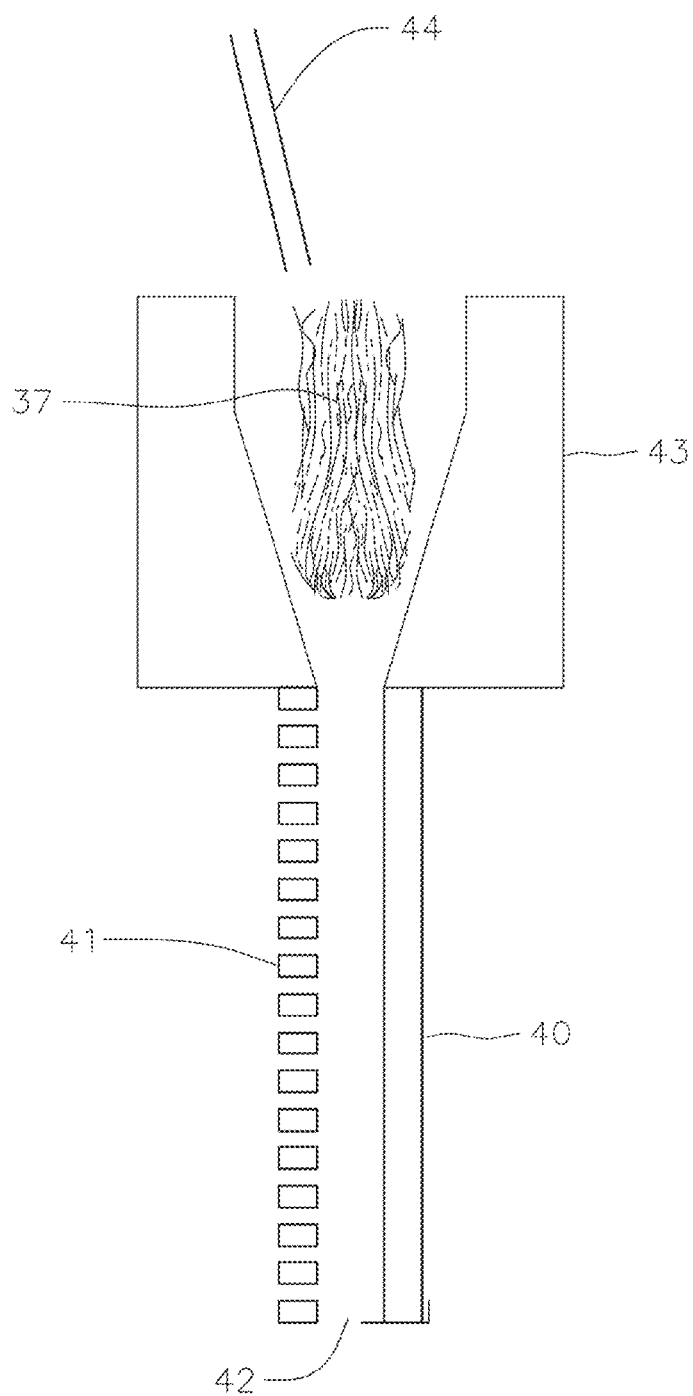
FIG. 17 shows a cross-section view of an apparatus for water jet assisted injection molding of DBF fibers, where the DBF fibers 37 are loaded into a hopper 43, the hopper being attached to a detachable mold 40, the mold tapered toward its distal end having vents 41 along its length, and a removable vented end cap 42, where the water jet 44 is activated to force the DBF from the hopper and into the mold, and the detachable mold is removed after DBF injection and placed into an oven or lyophilizer for drying, according to some embodiments of the present invention.

In some embodiments of the present invention, water jet assisted injection molding of DBF fibers is used. As shown in FIG. 17, the DBF fibers 37 are loaded into the hopper 43. The hopper is attached to a detachable mold 40, and the mold is tapered towards its distal end and has vents 41 along its length, and a removable vented end cap 42. A hand operated water jet 44 is activated to force the DBF from the hopper and into the mold. The detachable mold is removed after DBF injection and placed into an oven or lyophilizer for drying.

Figure 30D:
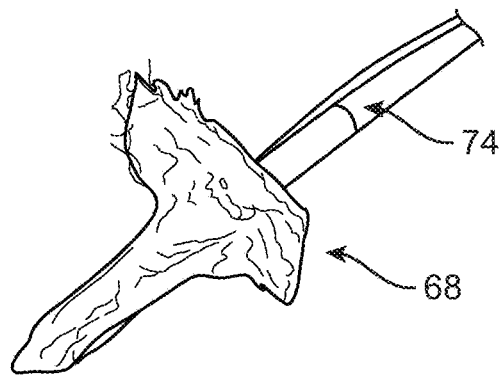

With reference to FIGS. 30*a* and 30*d*, the disclosed water assisted injection molding process may also be used to make the DBF implants such as the screw fixation device 68.

In more specific embodiments, the nozzle of the water jet is of between about 0.1 to 1 cm in diameter. Typically, the nozzle diameter is of between about 1 mm to 5 mm in diameter, and more typically, the nozzle diameter is of between about 2 mm to 4 mm in diameter. The fluid flow rate may be about 1 ml/minute, 30 ml per minute, or preferably up to about 1000 ml per minute.

The skilled person may easily envisage an apparatus with multiple funnels leading to multiple molds in a manner analogous to multi-cavity injection molds as used to fabricate injection molded polymer parts.

The implants of the present disclosure in their dry state may be inserted into a cavity, screw hold, awl hole, or drill hole. Additionally, the implants of the present disclosure may be housed in a syringe or syringe-like insertion device. With the implant in a syringe or syringe-like insertion device, the implant may have lateral stability thereby preventing or decreasing bending or buckling of the implant while it is being pushed into the surgical site (e.g., the cavity or hole).

In some embodiments of the present invention, entanglement of the DBF may be increased by stirring the fibers while in a liquid slurry. By creating a vortex, fibers are swirled and induced to become entangled. This entanglement results in non-woven 'ropes' of fibers that may be extruded and then cut to length and used as is, or further processed into pellets as described in this disclosure.

For the implants to swell post-implantation so that they are substantially space-filling, control of the processing conditions of the fibers may be controlled. For example, in some embodiments, the fibers are compressed, heated, and/or otherwise dried in order to render the fibers in a compact state such that upon wetting, the fibers are able to expand and swell.

In some embodiments of the present invention, an implant system package or implant kit includes the cylindrical molds and plunger as shown, for example, in FIG. 4.

Excipients and Additives

Additives are contemplated to modify biological or other properties of the implant according to embodiments of the present invention. Non-limiting examples of additives include growth factors such as bone morphogenetic proteins (BMPs), including BMP-1, BMP-2, BMP-3, BMP-4, BMP-5, BMP-6, BMP-7, BMP-8, BMP-9, BMP-10, BMP-11. BMP-12. BMP-13, BMP-15, BMP-16, BMP-17, and BMP- 18; Vascular Endothelial Growth Factors (VEGFs), including VEGF-A, VEGF-B, VEGF-C, VEGF-D and VEGF-E; Connective Tissue Growth Factors (CTGFs), including CTGF-1, CTGF-2, and CTGF-3; Osteoprotegerin, Transforming Growth Factor betas (TGF-βαs), including TGF-β-1, TGF-β-2, and TGF-β-3, and inhibitors for tumor necrosis factor (e.g., anti-TNF-α). Morphogens may also include Platelet Derived Growth Factors (PDGFs), including PDGF-A, PDGF-B, PDGF-C, PDGF-D, and GDF-5; rhGDF-5; and LIM mineralization protein, insulin-related growth factor-I (IGF-I), insulin-related growth factor-II (IGF-II), fibroblast growth factor (FGF) and beta-2-microglobulin (BDGF II), as disclosed in the U.S. Pat. No. 6,630,153, the entire contents of which is incorporated herein by reference. The polynucleotides encoding the same may also be administered as gene therapy agents. The preferred bioactive substances are the recombinant human bone morphogenetic proteins (rhBMPs) because they are available in relatively unlimited supply and do not transmit infectious diseases. In some embodiments, the bone morphogenetic protein is a rhBMP-2, rhBMP-4, rhBMP-7, or heterodimers thereof. BMPs are available from Wyeth, Madison, N.J., and may also be prepared by one skilled in the art as described in U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al., and WO94/26892 to Celeste et al., the entire contents of all of which are herein incorporated by reference.

Oxygenating additives such as perfluorocarbons may be used to further enhance the bone formation and healing of the DBF material in the implant of the present disclosure. In some embodiments, the bone repair DBF implant composition includes oxygenating materials such as a perfluorocarbon (PFC). In some embodiments, the DBF implant composition includes oxygen generating compounds such as peroxides (e.g., hydrogen peroxide, magnesium peroxide, calcium peroxide), perchlorates (e.g., sodium perchlorate, potassium perchlorate), percarbonates (e.g., sodium percarbonate), or perborates (e.g., sodium perborate).

For additional benefits, cancellous or cortical bone chips and/or demineralized cancellous or cortical bone chips may be added to the DBF. In addition to or alternatively to the bone chips, mineralized bone fibers may be added to the DBF. In addition to bone chips, mineralized bone fibers or alternatively, calcium phosphate, tri-calcium phosphate, hydroxyapatite, or other synthetic bone graft materials may be added to the DBF.

According to some embodiments of the present invention, introduction of an implant for screw augmentation into a patient is accomplished by placing the implant into a hole that has been drilled to receive a screw. The implant is sized to fit the hole to be repaired and to be space filling, i.e., the implant is of approximately the same length and diameter as the hole. The implant may be placed in the hole directly by hand or may be placed by use of a delivery instrument having a cylindrical element to hold the implant with a plunger to expel it. Accordingly, the delivery instruments may be cannulated.

In some embodiments of the present invention, the implant is longer than the depth of the hole to be treated and in these instances the surgeon may cut the implant to a desired length.

Forming an indentation into the end of the implant designed to receive the screw may facilitate central placement of the screw. Additionally, the implant may be cannulated or tubular to further facilitate screw placement over a guide wire.

In some embodiments of the present invention, implants are formed and stored in tubes. To facilitate loading into the end of the delivery tube a recess is formed in the end of the elongated member (e.g., cannula) to hold the storage tube in correct alignment.

In some embodiments a plurality of implants are stored in a holder that is configured to attach to a delivery tube to allow easy deployment of implants.

The delivery tube may be straight or curved. In the latter instance the plunger will be flexible, being made of any suitable material, for example, nitinol wire or braided nitinol wire.

The DBF implant may be shaped with a convex proximal end and concave distal end by the push rod. Alternatively, implants may be introduced by separate means into the end of the delivery tube. In some instances, implants having a pellet shape may be easier to introduce into delivery tubes.

At the time of surgery, prior to implantation, a small amount of any suitable water-soluble contrast agent may be injected into the implant to provide visualization during implantation. An example of a water-soluble contrast agent is Iopamidol.

At the time of surgery and prior to implantation, a small amount of sterile water, phosphate buffered saline, bone marrow aspirate, and/or blood may be injected into the implant to hydrate the implant.

EXAMPLES

The following examples use cortical human bone. As discussed herein, either human or animal bone may be used as a source of cortical bone. Fibers were produced using the methodology as described in U.S. Pat. Nos. 9,486,557 and 9,572,912, supra.

Example 1

1 ml disposable plastic syringes were used as a mold. The plungers were removed and 0.25 grams of DBF were introduced into the end of the syringe and the plunger used to lightly compress the fibers to a length of approximately 4 cm. The plungers were removed and the tip of the syringe cut off using a scalpel. The implants were vacuum dried overnight at 27° C. The resultant implants were approximately 4.5 mm in diameter Example 2

Three implants from Example 1 were used to test for augmentation of screw pull out. A Sawbones 10 pores per inch foam that is frequently used to test screw pull out as a surrogate for osteopenic bone was used. Six 5 mm diameter holes were drilled in the foam block. Implants from example 1 were placed in three of the holes. 5.5 mm pedicle screws were inserted into the six holes. An MTS tensile test machine was used to record the force required to pull the screws out of the holes. The data obtained are shown in Table 1 below.

TABLE 1

|  | Peak Force (N) | |
| --- | --- | --- |
|  | Control | Augmented |
| Test 1 | 346 | 764 |
| Test 2 | 338 | 868 |
| Test 3 | 290 | 778 |
| Average | 325 | 803 |

Example 3

15 grams of DBF fiber were wet laid in a 10 cm×11 cm flat mold to produce a sheet of DBF. The mold was heated at 55° C. for two hours to bond the fibers and dry the sheet. The sheet was approximately 1 mm thick. A portion of the sheet would be suitable for use in augmenting ACL or rotator cuff fixation.

Example 4

A portion of the sheet of Example 3 was cut to the shape of the tibial tray from a knee arthroplasty, hydrated and pressed onto the surface of the porous coated tibial tray.

Example 5

A portion of the sheet of Example 3 approximately 3 cm by 1 cm was hydrated and wrapped around the threaded portion of a 6 mm diameter pedicle screw. The DBF conformed to the surface of the screw.

Example 6

An apparatus to make implants using a water assisted injection molding (WAIM) was fabricated according to the schematic shown in FIG. 16. A 20 ml syringe with its distal end removed was placed in a 3D printed adapter. Three detachable mold sizes were used, each 5 cm long with diameters of: 3.5 mm decreasing to 3 mm; 4.5 mm decreasing to 4 mm; and 5.5 mm decreasing to 4.5 mm. DBF was placed in the 20 ml syringe and the syringe filled with PBS. The end of the syringe was placed in the adapter and the plunger pressed down to inject the DBF into the mold. DBF quantities used were 0.45 gram, 0.6 gram and 1.05 gram for the 3.5, 4.5 and 5.5 mm diameters respectively. After molding the molds were placed in a vacuum oven and dried under vacuum with a 0.5 L/min air flow overnight. After removal of the end caps the dried implants could be simply removed by pushing from the molds. The implant diameters were approximately 0.75 mm less in diameter than the mold diameter.

Example 7

A portion of the sheet from Example 3 was cut into two pieces each 2 cm×5 cm with a slot cut in it as shown in FIG. 25a. The sheets were then rehydrated and using four 3 mm diameter rods the cruciate form of FIG. 27a was formed. After drying the implant is shown in FIG. 27b. This implant was suitable for use in augmenting the fixation of an acl graft.

Example 8

A portion of the sheet from Example 3 was cut into one piece approximately 2 cm×5 cm. The sheet was then rehydrated and shaped using two 3 mm diameter rods and then redried. The implant of FIG. 27c was formed. This implant was suitable for use in augmenting the fixation of a two strand acl graft.

While the present invention has been illustrated and described with reference to certain exemplary embodiments, those of ordinary skill in the art will understand that various modifications and changes may be made to the described embodiments without departing from the spirit and scope of the present invention, as defined in the following claims.

Additionally, although relative terms such as "outer," "inner," "upper," "lower," "below," "above," "vertical," "horizontal" and similar terms have been used herein to describe a spatial relationship of one element to another, it is understood that these terms are intended to encompass different orientations of the various elements and components of the device in addition to the orientation depicted in the figures (Figs.).

What is claimed is:

1. A composition, comprising an implant for repair of a tendon-to-bone reattachment, the implant comprising:
    a plurality of fibers cut from demineralized bone, the plurality of fibers forming a contiguous shape having a peg portion and a sheet portion;
    wherein the peg portion has a cone or truncated cone shape with a distal closed end and a proximal open end;
    wherein the peg portion is capable of being inserted distal closed end first into a cavity of a bone;
    wherein the sheet portion is attached to and surrounds the proximal open end of the peg portion;
    wherein the sheet portion has a first side and a second side, and
    wherein, during use: the first side is in contact with an area on the surface of the bone adjacent the cavity, and the second side contacts the tendon, the sheet portion thereby forming an interface between the tendon and the bone.

2. The composition of claim 1, wherein the length of the peg portion is between about 10 to 50 millimeters (mm).

3. The composition of claim 1, wherein the diameter of the proximal open end is between about 3 to 10 mm.

4. The composition of claim 1, wherein the sheet portion comprises a circular shape, a perimeter of straight sides, a rectangular shape, a square shape, or an irregular shape.

5. The composition of claim 4, wherein each of the straight sides independently has a length of between about 5 and 20 mm.

6. The composition of claim 1, wherein the sheet portion has a diameter of between about 5 and 20 mm.

7. The composition of claim 1, wherein the sheet portion has a thickness of between about 0.5 to 5 mm.

8. The composition of claim 1, wherein the plurality of fibers are demineralized bone fibers (DBFs).

9. A method of augmenting reattachment of a tendon to a bone using the implant of claim 1, the method comprising:
    placing a suture anchor into the peg portion of the implant;
    optionally preparing a bleeding bone bed on the bone;
    creating a cavity in the bone;
    placing the peg portion of the implant into the cavity in the bone using the suture anchor with a suture driver;
    screwing the suture anchor into place; and
    using sutures to re-approximate and tie down the tendon to effect the reattachment of the tendon to bone.

10. A method of fabricating the implant of claim 1, the method comprising:
    dispersing the plurality of fibers in a fluid; and providing the dispersed plurality of fibers into a vented mold using pressure, thereby draining the fluid and forming the fibers into the shape of the mold, wherein the plurality of fibers are demineralized bone fibers (DBFs).

11. The method of claim 10, wherein a ratio of the DBF to the fluid is between about 1 gram of DBF to about 5 to 200 mls fluid.

12. The method of claim 10, wherein a ratio of the DBF to the fluid is between about 1 gram of DBF to about 5 to 10 mls fluid.

13. The method of claim 10, further comprising heating the plurality of fibers in the mold.

14. The method of claim 13, wherein the heating occurs at or between 35 to 55 degrees Celsius.

15. The method of claim 13, further comprising lyophilizing the heated plurality of fibers.

16. A kit for repair of a tendon-to-bone reattachment with an implant, the kit comprising:

the implant of claim 1.

17. The kit of claim 16, further comprising:

an awl or a tap; and a suture anchor.

18. The kit of claim 17, wherein the awl or the tap are disposable.

19. A method of augmenting a tendon to a bone reattachment, the method comprising:

placing the implant of claim 1 between the tendon and the bone.

20. A method of augmenting reattachment of a tendon to a bone using the implant of claim 1, the method comprising:

placing a suture anchor into the peg portion of the implant;

optionally preparing a bleeding bone bed on the bone;

creating a cavity in the bone;

placing the peg portion of the implant into the cavity in the bone using the suture anchor;

screwing the suture anchor into place; and using sutures to re-approximate and tie down the tendon to effect the reattachment of the tendon to bone.

21. A method of augmenting reattachment of a tendon to a bone using the implant of claim 1, the method comprising:

optionally preparing a bleeding bone bed on the bone;

creating a cavity in the bone;

placing the peg portion of the implant into the cavity in the bone;

inserting a suture anchor into the peg portion of the implant;

screwing the suture anchor into place; and using sutures to re-approximate and tie down the tendon to effect the reattachment of the tendon to bone.

22. A method of augmenting reattachment of a tendon to a bone using more than one implant of claim 1.

* * * * *